United States Patent [19]

Scheicher

[11] 4,279,598
[45] Jul. 21, 1981

[54] DENTAL HALF-IMPLANTS

[76] Inventor: Hans M. F. Scheicher, Rondell Neuwittelsbach 4, D 8000 Munich, 19, Fed. Rep. of Germany

[21] Appl. No.: 69,646

[22] Filed: Aug. 27, 1979

Related U.S. Application Data

[62] Division of Ser. No. 811,224, Jun. 29, 1977, Pat. No. 4,197,645.

[30] Foreign Application Priority Data

| Jul. 6, 1976 [DE] | Fed. Rep. of Germany | 2630400 |
| Jul. 6, 1976 [DE] | Fed. Rep. of Germany | 2630408 |
| Sep. 4, 1976 [DE] | Fed. Rep. of Germany | 2639887 |

[51] Int. Cl.$^3$ ............................................. A61C 8/00
[52] U.S. Cl. ................................................... 433/173
[58] Field of Search ..................... 433/173, 175, 201

[56] References Cited

U.S. PATENT DOCUMENTS

| 448,745 | 3/1891 | Wright | 433/175 |
| 2,835,035 | 5/1958 | Rauscher | 433/175 |
| 3,579,829 | 5/1971 | Sampson | 433/173 |
| 3,790,507 | 2/1974 | Hodosh | 433/173 |
| 3,971,134 | 7/1976 | Bokros | 433/201 |

FOREIGN PATENT DOCUMENTS

| 1958338 | 6/1970 | Fed. Rep. of Germany | 433/173 |
| 2157138 | 5/1972 | Fed. Rep. of Germany | 433/173 |
| 540713 | 3/1956 | Italy | 433/173 |
| 1341310 | 12/1973 | United Kingdom | 433/175 |

*Primary Examiner*—Gene Mancene
*Assistant Examiner*—John J. Wilson
*Attorney, Agent, or Firm*—Sughrue, Rothwell, Mion, Zinn and Macpeak

[57] ABSTRACT

The invention concerns a drill head for the attachment of bone drills or bone milling cutters, as well as the bone drills or milling cutters themselves, especially for preparing bone cavities into which enossal prosthetic elements can be inserted. The designation "bone drill" or "bone milling cutter" is meant to include all drills or cutters with which, in the field of human or veterinary medicine, including the dental field, material can be removed from teeth, bones and bone-like tissue, as well as from corresponding substitute materials. Finally the invention concerns also dental and half-implants, being particularly simply inserted with these instruments.

12 Claims, 70 Drawing Figures

Fig. 15
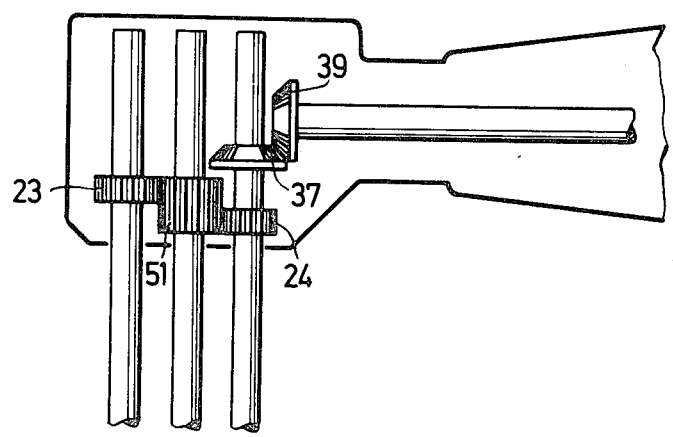
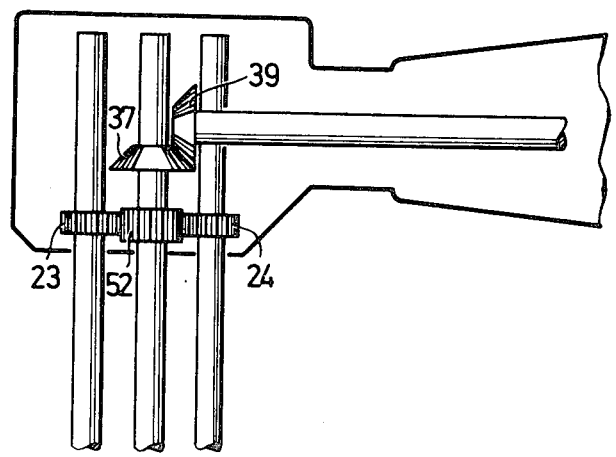
Fig. 16

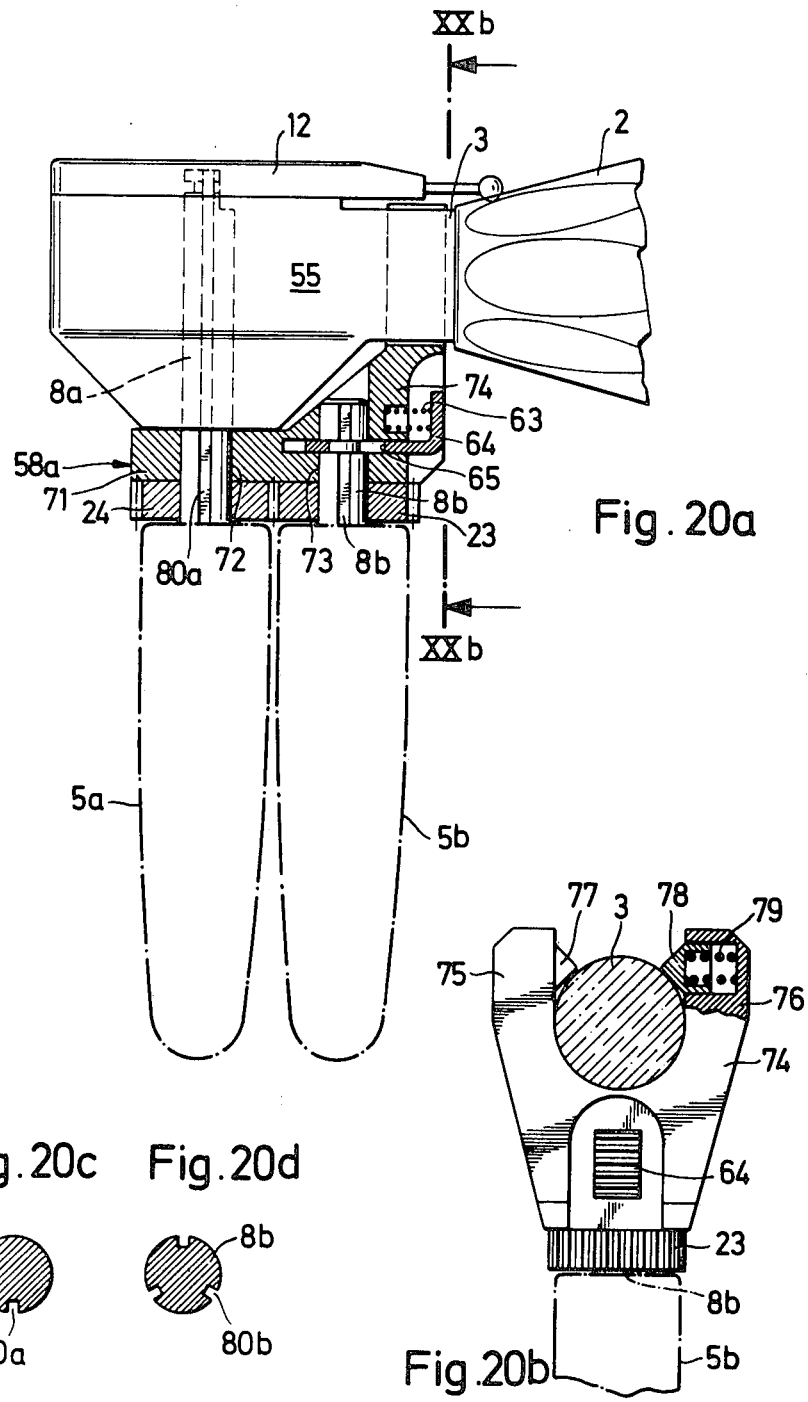

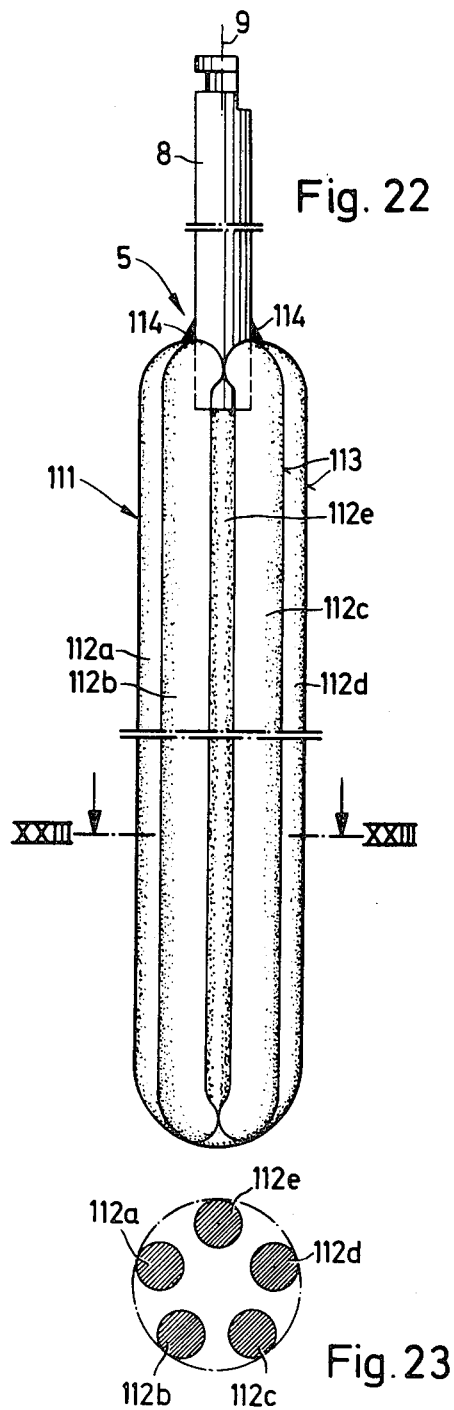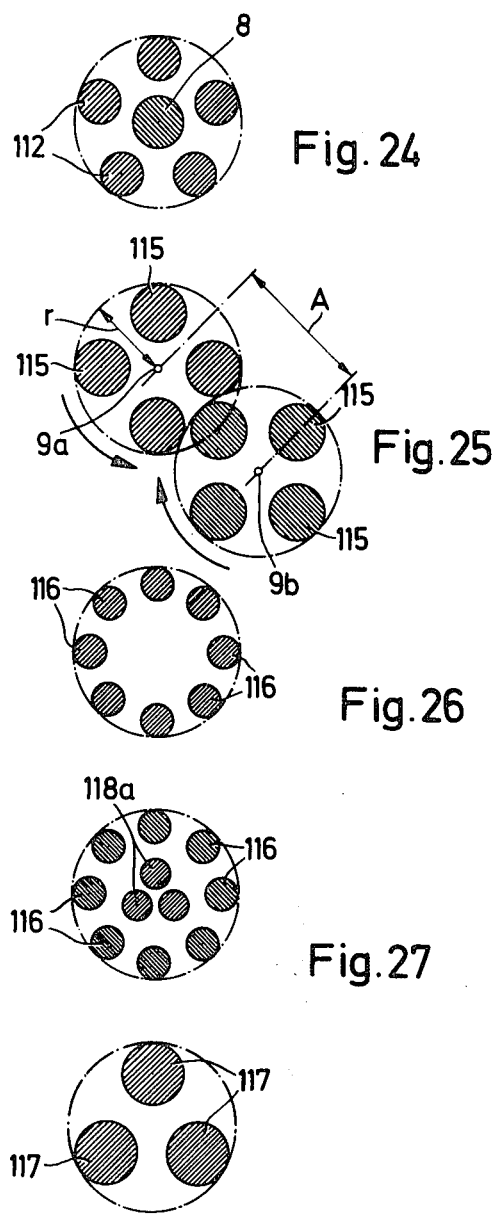

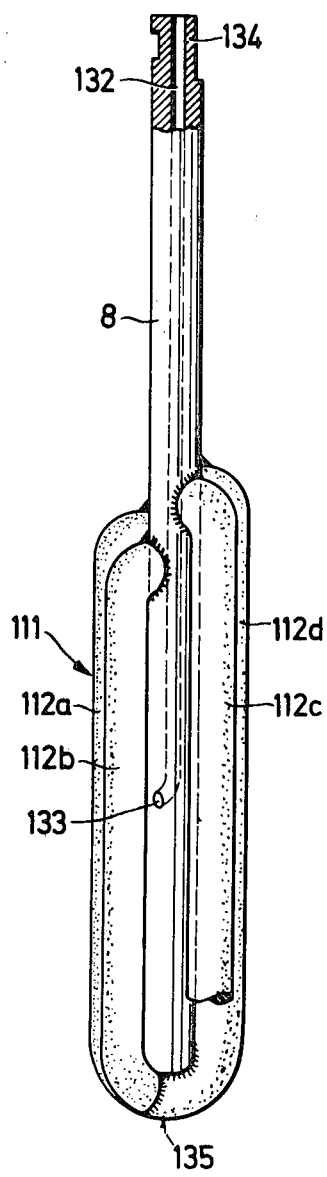

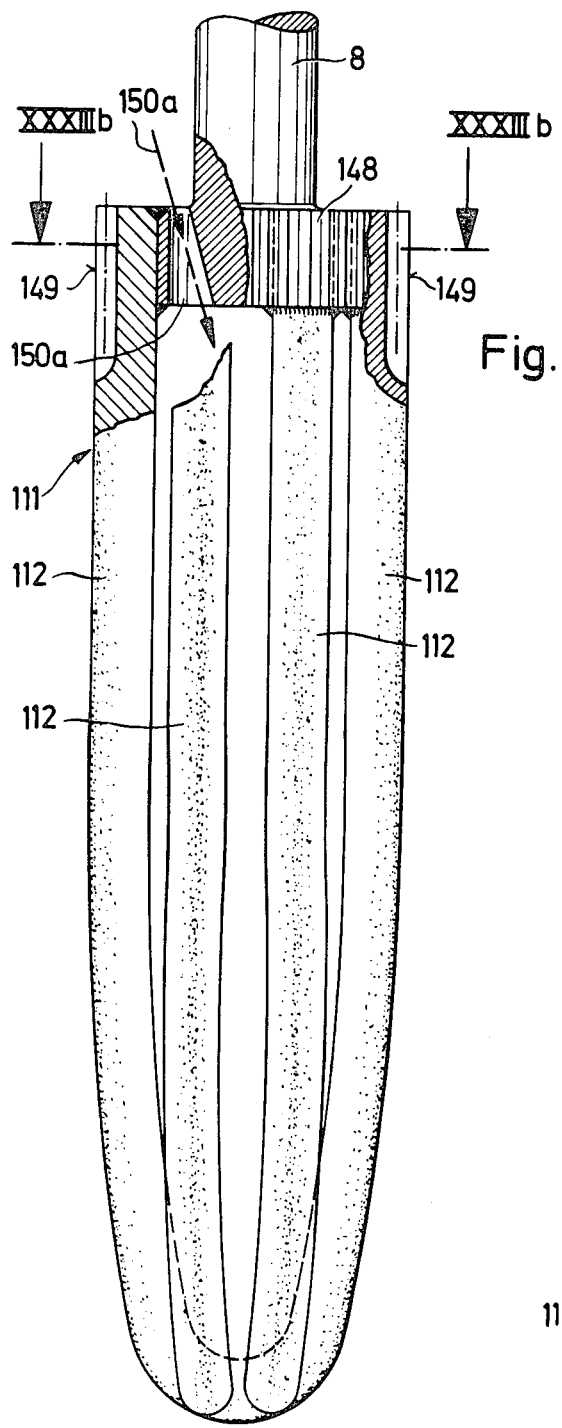
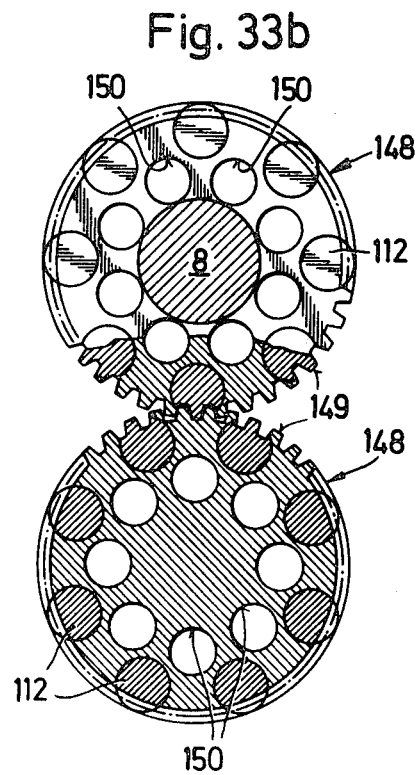
Fig. 33a
Fig. 33b

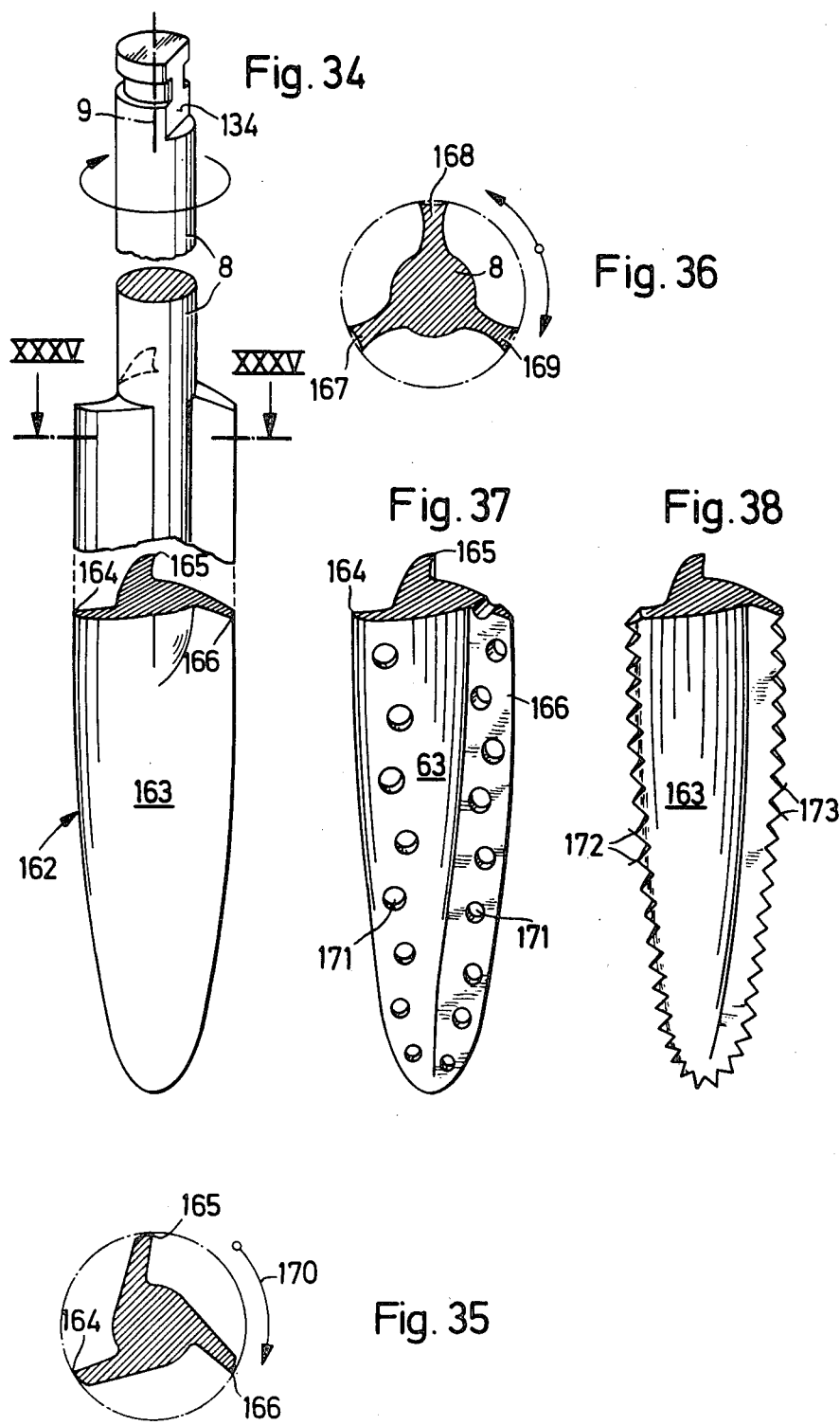

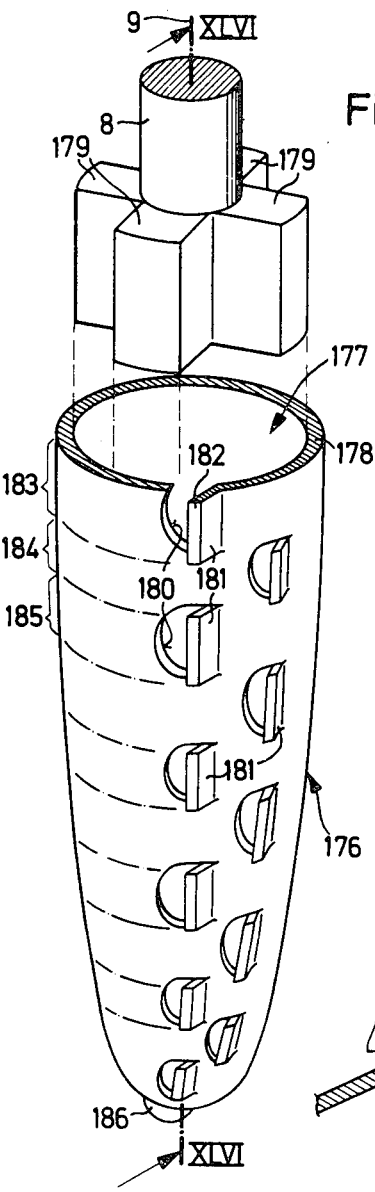
Fig. 41
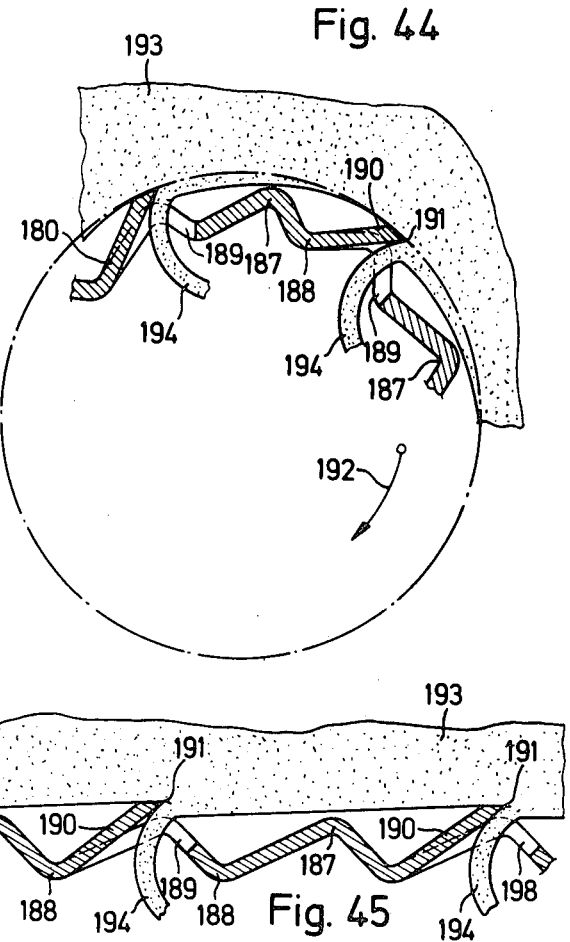
Fig. 44
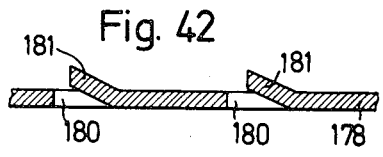
Fig. 42
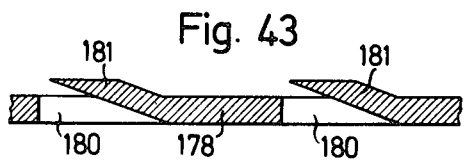
Fig. 43
Fig. 45

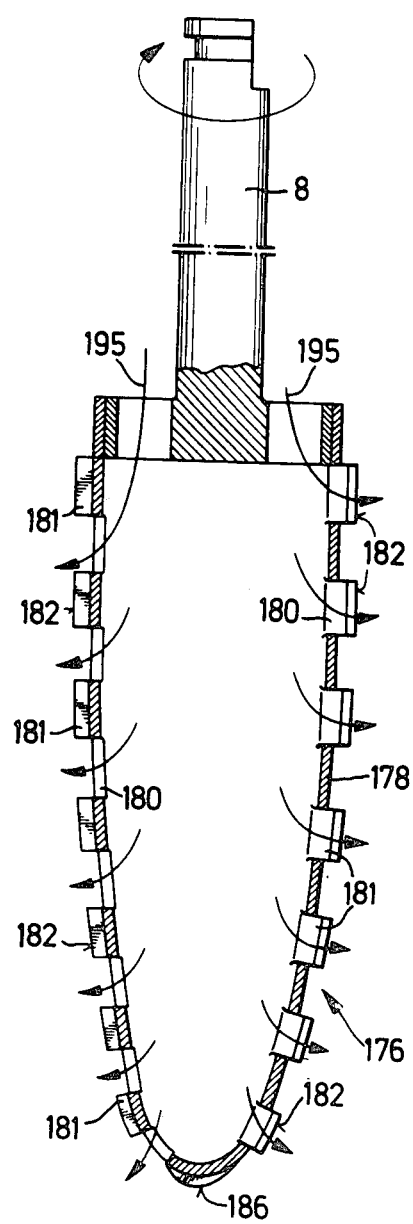
Fig. 46
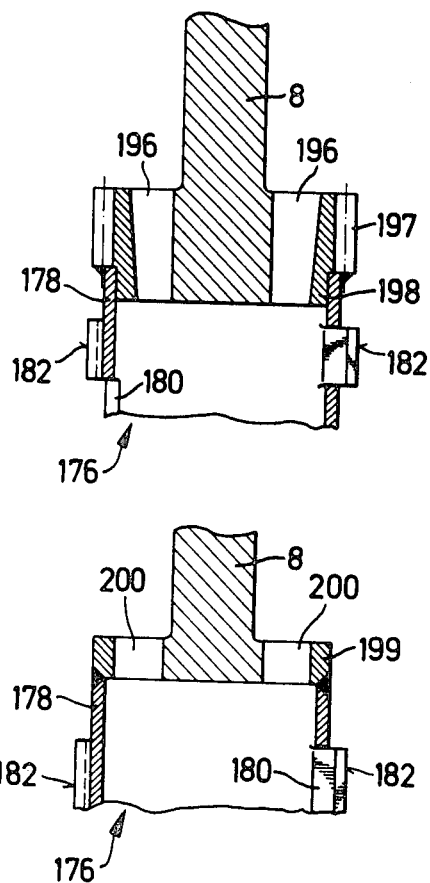
Fig. 47
Fig. 48

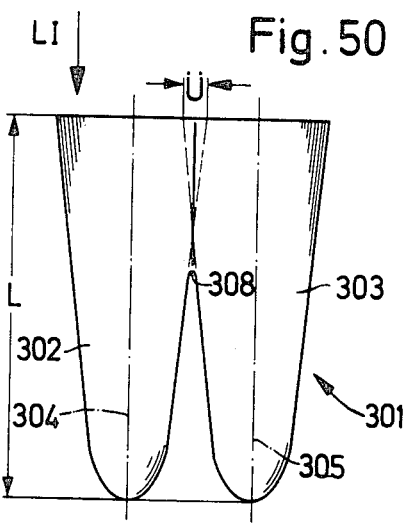
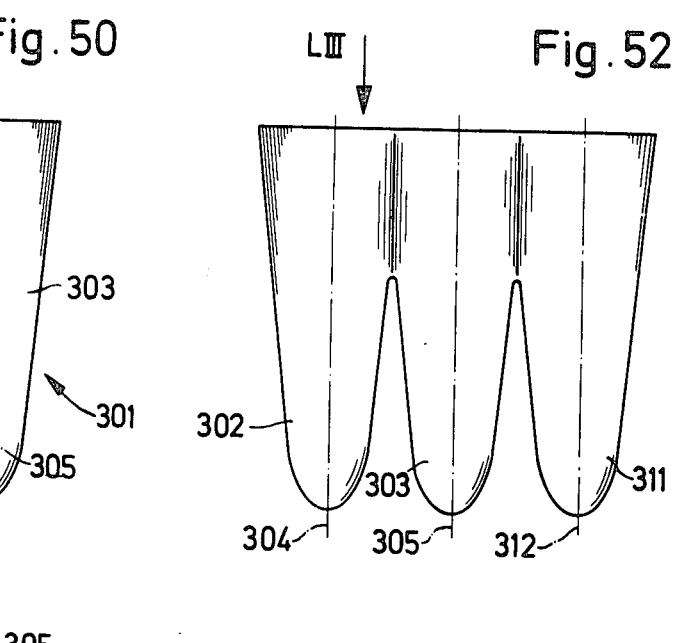

DENTAL HALF-IMPLANTS

This is a division of application Ser. No. 811, 224, filed June 29, 1977, now U.S. Pat. No. 4,197,645, issued Apr. 15, 1980.

Very accurate working is essential when making bone cavities for the insertion of enossal prosthetic elements so that the bone cavities exhibit the desired dimensions and the essential alignment. This applies in particular in the case of bone cavities designed for the insertion of dental implants. Additional problems arise here occassioned by the small extension of the jawbone, the teeth still remaining in it and the scant working space available.

Until now the production of large and exactly-shaped bone cavities has been effected free-hand using conventional drills and bone cutters normal in the field of dental medicine and surgery, these being mounted individually on corresponding drill heads. It is extremely difficult and time-consuming to create the desired bone cavities with these tools, and despite the use of markers, molds and templates one does not always succeed in achieving the necessary accuracy.

A considerable proportion of the failures with enossal implants can be attributed to the previously-mentioned difficulties. When for example the bone cavity is wider just in certain areas than the implant to be inserted, the danger of an infection between implant and bone wall is increased. In addition gum tissue invagination ensues in these areas, so preventing the bone tissue from growing together with the implant.

There is no known bone drill with which one can make deep, exactly-shaped bone cavities suitable for the insertion of implants in one operation. It is not even possible to make simple and exactly-shaped cylindrical holes in bones using the known drills, since the cutting heads are very short and shift during the drilling operation. There are as yet no long drills where shifting is prevented. This could be attributable to the fact that it is difficult to so eliminate the heat resulting during drilling or cutting that temperatures of 50° C. to 52° C., at which coagulation of the protein tissue occurs, are not exceeded. Cooling of the drilling region and of the drill with a cooling medium also becomes difficult with increasingly long drills.

The following publications are quoted as prior art:
DT-PS No. 360382
DT-PS No. 445682
DT-PS No. 711634
DT-PS No. 1255857
DT-AS No. 1018583
DT-OS No. 2331023
DT-OS No. 2419080
DT-OS No. 2543723
DT-GM No. 68037651
DT-GM No. 7215122
DT-GM No. 7322725
DT-GM No. 6803765

The following are in addition mentioned:

The use of common drill heads with corresponding special speed reductions and with small tolerances in the mounting, to guarantee a central passage of the cutter and a transfer of high pulling power to it. The use of fast-moving turbocutters, eg. the "Lindemann Cutter", for preparing the slots for laminar implants.

There are as yet no instruments enabling a simple, quick and accurate preparation of bone cavities.

The present invention has therefore the basic task of creating tools with which a simple, quick and accurate preparation of bone cavities, especially in the jaw region, is made possible. The invention has to do with the development of improved drill head constructions, with drills particularly suited to these purposes and being particularly suitable for use with these drill heads, and finally with particular enossal dental half-implants which are especially easily and advantageously inserted using the previously-mentioned instruments.

The drill head according to the invention for attachment of bone drills or cutters, especially for the preparation of bone cavities for the insertion of enossal prosthetic elements, is characterized by a mounting for at least two cutters having staggered axes of rotation, and by a driving mechanism for their joint operation.

The drill head according to the invention makes it possible to drill simultaneously with several cutters, whereby with a suitable refinement of the cutters the drill holes can overlap. Since the rotational axes of the individual cutters are positioned accurately with respect to one another, one obtains defined drill holes opening into another at least in the upper region and which, after removal, if necessary, of webs of bone tissue remaining between them, can form the desired bone cavities intended for insertion of prosthetic elements.

There is a further advantage in that any shifting of the individual cutter is avoided even when the bone tissue is very soft or brittle at one point, since there is at least one other cutter to take over the guidance in such a case.

The drill head according to the invention makes possible the production of a large number of bone cavities with defined but never-the-less varying shape since in the individual mounting of the drill head cutters of varying length, varying diameter and varying character of head can be used simultaneously in arbitrary combination. In this way bone cavities with a defined external contour, but being of varying depth in different regions can be made. The overlapping drill holes result in the side walls being dumbbell-like in cross section and where the implant is of corresponding shaping this guarantees an optimal and twist-free lodgement for the implant in the jaw, similar to that assumed by the natural tooth in the jaw.

Since it is not necessary to have the maximal number of possible cutters mounted at the same time when using the drill head according to the invention, it has universal application and can also be used where normally a drill or a milling cutter is adequate.

According to a first especially useful embodiment of the invention, being particularly suitable for working in the lateral area of the jaw branches, two cutters are attachable, one behind the other on the underside of the drill head and in the longitudinal direction of same.

According to a further embodiment of the invention, being particularly suitable for the inciser teeth region, two cutters are attachable at the front end of the underside of the drill head in such a way that the line connecting their axes of rotation runs essentially transverse to the longitudinal axis of the drill head. In a modification of this embodiment two cutters are attachable at the front end of the drill head in such a way that their axes of rotation are approximately in alignment with the longitudinal axis of the drill head. This modified arrangement is particularly economical to produce since the costly angular drive is unnecessary.

A torque compensation is obtained for the two driven cutters when the driving mechanism is so constructed that it sets the cutters contra-rotating. This advantage has the drawback that a clockwise- and an anticlockwise-drilling cutter must be used, these not being interchangeable with one another. To avoid confusion in this case, the mounting for the anticlockwise cutter and its shank is constructed differently to the corresponding structural element for the clockwise cutter.

A simple technical embodiment for the counter-rotational drive for two cutters is characterized by the driving mechanism having two cogwheels engaging with each other whose axes of rotation are in alignment with the rotational axes of the cutters and which either already are, or can be force- or form-locked with the cutter shanks, the one cogwheel being directly driven by these in a familiar manner. This driving mechanism is composed of few structural units and is attached in the head casing without wasting space.

Differentiation between clockwise and anti-clockwise cutters is unnecessary if the driving mechanism sets the cutters in synchronous rotation, as according to a further refinement of the invention. In an especially simple realization of this principle the driving mechanism has two cogwheels whose rotational axes are in alignment with the rotational axes of the cutters and which either already are, or can be force- or form-locked with the cutter shanks, whereby both cogwheels each engage with a third cogwheel and one of the three cogwheels is driven in a familiar way.

A further embodiment of the drill head takes care of the many problems arising through the necessity of being able to vary the distance between the cutter axes, so adapting optimally to the respective circumstances, in that at least one of the cogwheels is mounted in such a way that it can deviate. When it deviates, its axis of rotation describes a piece of a circular arc around the stationary rotational axis of the neighbouring cogwheel. It is most appropriate in this respect if the driven cogwheel remains fixed in position and at least one of the two cogwheels following can deviate. If however, as is the case with a somewhat more complex construction, both cogwheels following can deviate, it is possible to ensure that the longitudinal direction of the drill hole formed by the cutters retains the same orientation to the drill head, even when there is a shifting of the distance between the rotational axes. The orientation of the cutting direction does not therefore require any adjustment on the part of a drill head operator, an advantage not to be underestimated in view of the poor accessibility to the working area.

According to a further particularly advantageous embodiment, especially for the cheek teeth region, three cutters can be attached on the underside of the drilling head in such a way that their rotational axes constitute a triangle. The bone cavities created using suitable cutter configurations, the cavities being clover leaf-shaped in cross section, give correspondingly-shaped implants an excellent hold. The drill head can naturally also in this embodiment be operated with only a small number of cutters.

According to a further embodiment especially suited for the insertion of leaf-shape implants, three cutters can be attached one behind the other on the underside of the drill head and in its longitudinal direction, the rotational axes of the cutters thereby forming preferably a straight line or a curve approximately corresponding to the curvature of the mandibular arch. The three cutters are preferably driven by three cogwheels whose rotational axes are in alignment with those of the cutters, where the cogwheels are already in, or can be brought into form- or force-locking operative connection with the cutter shanks and where one of the cogwheels engages with the other two cogwheels. In this simple gearing two of the cogwheels are driven synchronously, the third contra-rotating, which must be taken into account when choosing the corresponding cutter.

A shifting in the distance between the individual rotational axes can be achieved if the rotational axis of the cogwheel engaging with the other two cogwheels is stationary, and the rotational axis of at least one of the two other cogwheels can deviate along a circular arc whose center is the rotational axis of the fixed cogwheel.

The problems possibly arising from the differentiation between clockwise- and anticlockwise-rotating cutters can be avoided if the driving mechanism sets the three cutters in synchronous rotation. This is effected preferably by means of an idler gear engaging with each of the three cogwheels setting the cutters in rotation.

According to a further particularly useful refinement, two idler gears are provided, these engaging with the first and the second, or respectively the second and the third cogwheels setting the cutters in rotation. The last-mentioned embodiment is preferred when the rotational axes of the cutters should be shiftable in such a way that they exhibit for one, a triangular, for the other a straight line conformation. This adjustability is usefully achieved by having at least one of the cogwheels, with which only one idler gear engages, able to deviate around this idler gear in such a way that the rotational axis of the deviating cogwheel describes a piece of a circular arc around the center of the corresponding idler gear.

A uniform instrument with smooth surfaces easy to clean is obtained when the mounting for all the cutters is attached in the interior of the drill head casing. An arresting chuck affording a force-locking mounting is particularly suitable for cutters with thicker shanks, which should transmit high moments of rotation. Such a chuck is preferably fitted in a familiar way with a drill mounting cover which can deviate about an axis and which grips in a hook-like manner into slots at the upper ends of the shanks.

A form-locking mounting afforded by a chuck is useful particularly when using FG-drills or corresponding cutters.

For handling the drill head it is particularly practical if all structural units of the driving mechanism are accommodated in the interior of the head casing. The driving mechanism has preferably a toothed-wheel gearing arranged at the bottom of the head casing, allowing a freely-rotating connection between the cutters, and a familiar bevel-gear drive which drives the spur gearing. This refinement enables the total height of the drill head to be small and the cutter shanks to be guided exactly in their inlet area in the drill head. The cutters are guided exactly by means of a construction whereby the cogwheels are provided on their upper side with axle-tube-like sleeves and are guided by means of bearings at the bottom of the head casing and/or above the sleeves at the top in the head casing. The axle-tube-like sleeve is preferably provided at its upper end with an attachment projecting inwards which grips in a form-locking way in a slot or at a flattening of the shank of a cutter introduced into the sleeve. The shank is preferably guided in the interior of the head housing by a bushing, this being positioned in the underside of the head casing and extending inside the axle-tube-like sleeve to underneath the inwardly-projecting attachment which effects the driving of the cutters. The bushing can thus serve as the lower bearing for the cogwheel. The axle-tube-like sleeve is preferably held at its upper end externally in a guide bearing.

According to a further embodiment especially suited for a mounting for FG-cutters the axle-tube-like sleeve is constructed as an adapter sleeve. In comparison to the previously-mentioned construction this one involves fewer component parts. By means of a one-piece construction of the cogwheel and the axle-tube-like sleeve, very accurate guiding can be achieved.

A bevel pinion is preferably connected with one of the axle-tube-like sleeves in the upper region, this bevel pinion engaging with a pinion which is attached at the end of the drill head driving shaft.

According to a further refinement of the drill head according to the invention the driving mechanism is furnished with a gear unit arranged at the top of the head casing and connecting the cutters with one another so that they rotate freely, and a familiar bevel-gear drive which drives the gear unit. This refinement is particularly reccommended when alterations of the transformation ratio are desired. It is practical if the bevel pinion is rigidly connected with one of the cogwheels of the spur gearing or else forms a part of the same.

In a further particularly preferred embodiment of the drill head according to the invention a bevel-gear drive is attached in the head casing whilst a gear unit, which allows a freely-rotating connection between the cutters, and/or the mounting for at least one cutter are arranged outside the head casing. This embodiment enables one to adapt to conventional drill heads without having to change their drive or their head casing. Such a changeover is effected preferably through use of an adapter which connects releasably with a conventional drill head for the attachment of a drill or milling cutter, and which, also after the changeover, forms the mounting for the shank of at least one cutter. The adapter is usefully constructed as an insert unit which can be attached to the underside of the conventional drill head in such a way that the one cutter has its shank inserted into the conventional drill head and is set into rotation. The adapter renders at the same time a releasable mounting for at least a second cutter. The adapter is appropriately connected with the conventional drill head by means of an attachment element which can be releasably inserted into a recess in the insert unit and which attaches to the wall or to the upper side of the conventional drill head. In addition can arrest is reccommended, this preventing any twisting of the adapter relative to the conventional drill head.

An especially small constructional embodiment of the adapter results when the adapter has a forked arm projecting upwards which attaches to the neck of the conventional drill head and is held arrested there.

It is especially favourable if a part of the adapter lying opposite the underside of the conventional drill head can deviate around the rotational axis of one of the cutters inserted in the conventional drill head. In this respect an arresting mechanism is preferably employed which releasably fixes the swingable part of the adapter is discrete angular positions.

The swingable part of the adapter consists preferably of a plate, exhibiting in its middle region an opening for the shank of a cutter to pass through, and being equipped at its edge with a series of connecting elements, these being releasably engaged with an accompanying connecting link of the forked extension; the releaseable mounting for the shank of at least a second cutter is attached on the region of the plate which is, with respect to the opening, opposite the connecting elements.

When a conventional drill head is to be adapted, it is sometimes advantageous if the gear unit, which connects the cutters with each other is a freely-rotating manner, is furnished with cogwheels being rigidly attached to the shank of the cutters and being removable, together with the cutters, from the drill head. In this way the intervals can be easily altered especially if also the mounting attached in the plate for at least one further cutter is adjustable. The cogwheels are preferably positioned on the upper edge of the cutters or else form the upper edge of same.

According to a further embodiment, the gear unit affording freely-rotating connection between the cutters, is attached in the adapter. Finally it is favourable if at least one nozzle is provided on the drill head for transmitting a cooling medium to the cutters and/or the respective working area. The nozzle is attached usefully in such a way that it delivers the cooling medium between the cutters and/or in the case of hollow cutters, into the interior of same.

For most areas of application it is desirable for the mounting to support the shanks of the cutters in such a way that their rotational axes run parallel to one another. The gear unit, affording a freely-rotating connection between the cutters, is in these cases preferably a spur gearing. Cases of application are however foreseeable where a mounting might be preferred which supports the shanks of the cutters in such a way that the rotational axes of at least every two cutters intersect. In such a case a bevel gearing serves preferably as the gear unit affording a freely-rotating connection between the cutters.

It is further useful to so construct the driving mechanism for the cutters that it enables the selective standstill of at least one of the cutters fixed in the drill head, whilst the other cutters rotate. The cutter standing still can serve as template or guide for the continued drilling process where at least one cutter is still rotating.

The present invention has also the special basic task of creating bone drills which offer good cooling and rinsing potential and which in an arrangement of at least two drills, having staggered axes of rotation and being fixed in the previously-described drill head, make possible in one operation the production of deep, exactly-shaped bone cavities from at least two partly-overlapping cylindrical or cone-shaped holes.

This task is fulfilled according to the invention by a bone drill especially for the preparation of bone cavities for the insertion of enossal prosthetic elements, the drill being characterized by a combination of the following features:

the length of the cutting head corresponds to at least the maximal depth of the bone cavities to be bored;

the boring bits are, at least in the upper region of the cutting head, arranged along curves running in planes which contain the rotational axes of the drill shank;

the cutting head is provided with deep recesses between the bits, which at least in the upper region of the cutting head, enable a meshing of the drill bits and the bits of a symmetrical but contra-rotating cutting head;

the cutting edge of a bit runs through the drill point.

The drills according to the invention can be used individually for the production of blind hole bone cavities, whereby their deep recesses between the bits enable the drilling site to be well supplied with a cooling- or rinsing liquid. The considerable length of the cutting head renders the desired guidance in the drill hole. The particular advantages of the drill construction according to the invention are however really effective when several of the drills are held simultaneously in a drill head, the drills having their axes of rotation suitably staggered in relation to one another. With an arrangement of this sort, a large number of bone cavities of defined but varying shape can be produced, since in the individual mountings of the drill head drills of varying length, diameter and character of head can be simultaneously used in arbitrary combination. In this way bone cavities having a defined external contour but exhibiting various depths in different areas can be produced. The overlapping drill holes result in the side walls being dumbbell-shaped in cross section, and where the implant is of corresponding shaping this guarantees an optimal and twist-free lodgement for the implant in the jaw, similar to that assumed by the natural tooth in the jaw.

In a particularly advantageous embodiment of the bone drill according to the invention the boring bits of the drill are formed from at least two rods being distributed over the extent of the cutting head and running in planes containing the rotational axes of the drill, the rods being provided on their outer surfaces with cutting edges, a toothing or a diamond finish. The rods are so dimensioned and mounted that they form a lattice enclosing a cavity, this being open to the exterior for the passage of a cooling- or rinsing medium and for the borings at least at the sides of the drill above spaces between the rods, and/or at the upper side of the drill.

According to a preferred refinement the rods have a polyhedral cross section, whereby in each case one or two of their edges point outwards and are formed into cutting edges which describe circles running normal to the rotational axis. On account of their polyhedral conformation defined guide surfaces arise for the borings and the cooling medium as well as additional edges also in the interior of the drill, which bring about the distribution of the borings and their removal.

It two of the edges point outwards and the inward-running surfaces from these two cutting edges of a rod run symmetric to a plane which contains the rotational axis, then the same drill can be used clockwise and anti-clockwise. This is useful for the production of bone cavities of at least two overlapping cylindric or cone-shaped holes, where the one drill is used anti-clockwise and the other clockwise.

In the case of drills which, contrary to this, are provided with one bit orientated in one direction, care must be taken when inserting into the drill head that in each case an anti-clockwise and in each case a clockwise corresponding drill is accommodated in the accompanying drill head bushing.

The lattice-like rods enclosing the cavity are preferably round bars whose diameter measure about 15% to about 40% of the cutting head diameter. In the case of drills tapering cylindrically the rods can taper in the direction of the drill point, preferably approximately proportional to the decrease in the cutter head diameter.

In a preferred refinement of the bone drill the rods run together at their lower ends, in the point of the drill, whilst at their upper ends they are attached to the drill shank.

If the lower end of the drill shank ends in the region of the upper ends of the rods, or if the drill shank is formed in the interior of the drill by a number of thin rods, a particularly good cooling- and rinsing potential results.

In a further embodiment to make better use of the entire diamond-finished surface of the rods, these can rotate about their own longitudinal axes in at least one area forming the side wall of the cutting head.

In a further construction of the bone drill according to the invention there are two, preferably three bits provided, being orientated at 120° to each other and working in the same direction, and being furnished with a diamond finish and/or with a toothing, these bits standing out wing-like from the shaft of the drill and each exhibiting at least one cutting edge which runs in one of the planes containing the rotational axis of the drill. At least one cutting edge runs through the drill point. The areas of the drills standing out wing-like from the drill shaft and provided at the ends with the bits are preferably furnished with perforations. This measure reduces the rotating masses and brings about turbulence and thus the rinsing effect of the cooling medium introduced. The toothings of the bits are staggered in order to attain an optimal cutting effect.

If the areas standing out wing-like from the drill shaft run curvedly in the direction of rotation, each having a cutting edge on their front side, a particularly good spatial effect results. It is however necessary in this case to use two drills constructed homologously with respect to the cross section for the production of bone cavities with overlapping drill holes. This disadvantage is avoided if the areas projecting wing-like from the drill shaft run radially outwards and are provided at the edge with two cutting edges being symmetrical to their centers.

In a third basic construction of the bone drill according to the invention a thin-walled hollow body is provided, being at least partly open on its upper side, being connected with the drill shank and corresponding shape-wise to the outer contour of the cutting head. This hollow body contains numerous prominences in the outer areas coming into contact with the drill hole, these prominences exhibiting sharp-edged openings pointing in the rotational direction of the drill and leading to the interior of the hollow body. With this slotted construction of the bone drill the sheared-off bone chips come into the interior of the hollow body, from where they can in turn issue out via its open area at the top. The hollow body, being partly open on its upper side, can also be acted upon easily by a cooling- or rinsing agent which can then pass outwards from this through the sharp-edged openings in the areas where chip removal is occurring.

The prominences surround the hollow body preferably following one another as a ring in the direction of rotation, whereby the prominences of two neighbouring rings are opposed to holes. This arrangement makes it possible for a clockwise or an anti-clockwise rotating bone drill to mesh with their bits in the case of the drill being driven in the contra-direction.

The prominences and/or the cutting edges formed by their openings pervade preferably, at least in the upper region of the cutting head, planes which contain the rotational axes of the drill. If a large overlapping of the drilling areas is desired the hollow body is provided at least in the upper region with cutaway portions running in the longitudinal direction of the cutting head and which extend over a considerable number of rows of prominences. The meshing of the drills is thus not limited to those stretches with which the bits protrude above the periphery of the hollow body. If bone cavities are to be made where at least two cylindrical drill holes should be superimposed until approaching their points, their being achieved by inclining the drilling axes, the bone drills are constructed in such a way that the cutaway portions extend almost to the drill point and account preferably for approximately a quarter to approximately a half of the cutting head circumference.

Particularly smooth surfaces of cut are obtained if the forward edges of the prominences, acting as cutting edges, are ground parallel to the wall of the hollow body. To improve the coolant circulation and the removal of the sheared off bone chips the hollow body is usefully furnished with perforations, which, seen in the rotational direction, lie in front of the prominences and open into their apertures. The apertures are thus extended in the rotational direction in order to facilitate the introduction of the bone chips into the hollow body.

The hollow body of the previously-mentioned bone drill is preferably constructed in a corrugated fashion whereby the cutting edges lie in the region of the ridges. Its ridges and troughs preferably form curves lying in planes which contain the rotational axis of the drill. It is particularly favourable if the cutting edges are constructed on every second consecutive ridge and/or by turning up areas of the ridges are formed along U-shaped incisions in these. It is appropriate that a cutting edge passes through the drill point.

When the bone drill according to the invention is intended for the production of bone cavities for the insertion of dental implants, the length of the cutting head measures preferably about 10 mm to about 25 mm and the maximal diameter about 2 mm to about 8mm. For the previously-mentioned purpose it is particularly useful if the cutting head tapers conically over about three quarters to about two thirds of its longitudinal extension, then being shaped cylindrically for approximately the last quarter or third facing the point.

The angle between the cone-shaped shell and the rotational axis of the cutting head is preferably about 4° to about 15°.

For the reasons already mentioned it can be useful if a cogwheel is fixed, or can be fixed on the upper side of the cutting head, the cogwheel being supplied with perforations or holes in order not to impair the rinsing and cooling effect.

The drill shank is for this preferably provided with at least one continuous longitudinal groove and/or a projection positioned above the cutting head, thus enabling a freely-rotating insertion of a cogwheel, itself being also furnished with a projection and/or a groove in its axle shaft. The drills can thus be used in drill heads where all chucks for the drill shanks are driven, as well as in such drill heads containing only one mounting for the various drills but only one drive for one of these. By pulling off the cogwheel it is further possible in the case of the last-mentioned construction, to leave one of the drills being supported in the drill head in standstill, whereby the stationary drill can serve for example as guide in an already-existing drill hole.

Finally it is useful, in the case of drills with large diameters, to furnish their shanks in a familiar way with an inlet opening to the interior of the cutting head for a cooling or rinsing medium.

The drill shank is usefully furnished with at least two annular tee-slots being staggered in the direction of the rotational axis, so that the bone drill can be held in a drill head at different points on the shank.

The invention concerns in addition an enossal dental half-implant, being especially easily and safely inserted using the previously described instruments. Since the exact physiologic relationships are not yet fully clear, a large number of enossal dental half-implants have already been developed and put forward, over whose suitability, however, opinions vary strongly. Above all, the success quotas are very different also for the single implant types. A general review of this prior art is given in a dissertation by Johannes Randzio of the Medizinische Hochschule Hannover (clinic and outpatient department for jaw surgery), excerpts from which are also to be found in the Zeitschrift Orale Implantologie, journal 4, 1976, pages 9 ff. The present application also bases on the nomenclature used there. With respect to the definitions of the individual concepts reference is made to the explanations given in the dissertation.

The dental half-implants currently most in use are the screw implant, especially according to Dr. S. Sandhaus (exemplified in a prospectus from the firm Maret with the title "Implant endo-osseux CBS"), the so-called "Tubinger Sofortimplantat" or immediate implant (described in the magazine "Quintessenz" 27. volume June 1976, journal 6, pages 17 ff.), the vitreous carbon implants (for example the Vitredent-Implant developed by the University of Southern California and described in a brochure put out by them), the laminar implants according to Linkow and consisting of an elongated leaf-like endostructure furnished with perforations and having a projection at the top for the fitting on of the tooth superstructure. Implantation of the laminar implants made of titanium alloys is carried out in two stages. There is a series of further developments of laminar implants, eg. the so-called "Zylinderimplantat" (article by Werner Lutz in "Die Quintessenz", 27. volume, February 1976, journal 2, pages 23 ff.) and laminar implants which are coated with a porcelain layer in order to avoid metallsis (DT-OS No. 24 21 951).

The present invention has the further task of creating an enossal dental half-implant with a large surface and good retention of the endostructure in the bone tissue. The implant should be free of sharp edges, at which centers of force are transmitted to the bones. It should oppose any distortion, tilting or loosening through any forces acting asymmetrically on it, especially shearing forces, and can also be used where the bone tissue is in parts bad or receding, especially at points on the lower jaw where the jawbone above the nerves or vessels is not thick.

This task is solved according to the invention by the endostructure of the implant having at least two cone-like regions overlapping at least in the area where the endostructure extrudes from the jawbone, and being separated from one another at their lower ends.

The enossal dental half implant (abbreviated to EDH in the following) as according to the invention is stably anchored in the jaw by the separation of its lower ends and by the constrictions in and below the area where the endostructure extrudes from the jawbone, these constrictions resulting from the overlapping of the cone-like regions, so that the implant is not loosened even by shearing forces arising from non-uniform loading, but without the individual areas of the bone having to accommodate too great forces.

In addition to EDH according to the invention offers the possibility to bypass nerves or vessels by means of a corresponding orientation in the jawbone, so that these are between the separated lower ends of the cone-like regions. It is also possible to bypass bad or weak points of the bone tissue in this way. The shaping of the EDHs according to the invention in the upper region where it extrudes from the jawbone makes it possible to leave the implant in position also in the case of shrinkage of the jawbone and of the gum, without any cosmetic problems arising.

Should it at some time become necessary to remove the implant from the jawbone, no large lesions are created when it is taken out.

It is especially useful if the endostructure exhibits a dumbbell- or double dumbbell-shaped cross section, at least in the area of extrusion from the jawbone. Surfaces of cut of the EDHs which have planes running approximately normal to the longitudinal axis of the tooth substitute borne by the endostructure are designated here as cross section. The longitudinal axis coincides approximately with the direction of the force applied to the tooth during the normal chewing process. Under the designations "dumbbell-like" or respectively "double dumbbell-like" such cross sectional shapes are to be understood which arise from the overlapping of two, or respectively three consecutive circles, ovals or ellipses; those points at which the circles, ovals, or ellipses intersect are rounded off in order to avoid sharp edges.

It is particularly advantageous if the cone-like regions of the endostructure, there being at least two such regions, are together elliptical, oval, or circular in cross section, and if the edges and/or the points arising where the individual regions overlap are rounded off. The last mentioned measure prevents very high pressure forces from acting on discrete bone regions. These forces could cause the bone to recede.

The center points of the cross sectional areas of the cone-like regions, there being at least two such regions, lie preferably on straight lines which form the axes of the cone-like regions. The cone-like regions are usefully limited at the sides by conical surfaces. This construction is particularly favourable since by means of the previously mentioned meshing drills and the corresponding drill heads, which can hold several of these meshing drills at once, bone cavities which correspond to these EDHs true-to-shape can be produced in the jaw through simple sinking. This effects not only a lodgement being stable against any distortion for the EDHs, but also reduces the danger of infection.

The bone cavities are especially easy to make if the axes of the cone-like regions run parallel to one another. For special cases of application and for adapting to peculiarities of the jawbone it can however be useful to let the axes of the cone-like regions run inclined to each other. If, however, the EDH consists of only two cone-like regions, then the axes lie preferably in one plane.

If the axes of two cone-like regions intersect beneath the endostructure in a pointed angle $\alpha_1$, especially if the angle $\alpha_1$ is so chosen that an overlapping of the cone-like regions occurs shortly above their lower ends, one obtains EDHs which are particularly suitable for use as inceser or eye-teeth.

If on the other hand the axes of two cone-like regions intersect above the endostructure in a pointed angle $\alpha_a$, one obtains EDHs which are particularly suitable for cheek tooth implants since they have several largely independent "tooth roots", as in the natural cheek teeth. This construction makes possible a substantial bifurcation between the cone-like regions, so that the implant can have its lower ends led deep into the bone, even when there is a nerve strand lying high up, the nerve strand coming to lie in the bifurcation between the two cone-like regions in this case. With respect to a production of bone cavities by simple sinking, by means of a suitable tool, it is particularly useful in the angle $\alpha_a$, which incorporates the two outermost cone-like regions with each other, is large enough to fit the following relation:

$$\alpha_a \leq \beta_1 + \beta_2$$

where with $\beta_1$ and $\beta_2$ the angles are designated which the cone-shaped shells of the cone-like regions enclose with the axes of same.

It is particularly favourable for the transmission of force to the bone structure if the angles bounded by the cone-shaped shell and the axis, being in the cone-like region, are between about 4° and about 15°.

The overlapping Ü between two cone-like regions in the EDHs according to the invention suffices preferably for the following relation:

$$0.15 \times D \leq Ü \leq 0.75 \times D$$

where with D the largest diameter of the cone-like regions forming the endostructure is designated. As overlap the distance is designated over which the cone-like regions overlap along the lines connecting the points where the axes of the cone-like regions cut through the cross sectional area at the region of the endostructure's extrusion from the jawbone. By keeping to these relations bone cavities can still be produced in one operation by sinking, using corresponding special drills and cutting heads.

According to a particularly useful structure of the EDHs according to the invention, the cone-like regions of the endostructure taper conically over some three quarters to some two thirds of their length, then being shaped cylindrically at their lower ends over some ¼ to ⅓ of their length.

For most fields of application one obtains excellent results if, for the conical parts of the cone-like regions, the relation of the greatest diameter D to the smallest diameter d is about 1.4 to about 4.0, preferably about 1.6 to about 1.8.

For some areas of application, specially when it is not possible to produce deep bone cavities in the jaw, one is reccommended to arrange three cone-like regions lying in a triangle beside each other in such a way that two of these regions touch each other whilst each at the same time intersects with the third. Using a special drill head and three special corresponding drills a bone cavity for this EDH can also still be produced in one operation by sinking, so that one obtains a very accurately-shaped and exact skeleton-form which corresponds to the outer contour of the EDH to be implanted.

The individual cone-like regions of the EDHs according to the invention can fundamentally be of varying length and/or exhibit varying diameters in the same cross sectional planes. Through the use of corresponding drill combinations suitable bone cavities can be produced in these cases too by simple sinking. In general, however, unless there are special circumstances in the jaw to be considered, EDHs are preferable where all the cone-like regions of the same formation. This simplifies insertion and prevents errors occurring when clamping the corresponding drills.

The longitudinal extension of the EDHs is usually measured such that on insertion into the jaw the upper edge of the endostructure is flush with the upper edge of the jaw ridge.

The endostructure is provided on its upper side with some kind of conventional attachment for fixing on the artificial tooth superstructure. In a special modification of the EDHs according to the invention, the endostructure contour is continued or extended upwards in the region of the exostructure. When inserting these EDHs thhe bone cavity is drilled to the desired depth and the EDH inserted by trial. The area projecting above the bone ridge is then trimmed in such a way that it forms the basis for the conventional construction of an artificial tooth, such as, for example, a jacket crown or a metal ceramic construction. The implantation of the EDHs according to the invention can follow in one or in two stages.

In a further refinement of the EDHs according to the invention the endostructure and/or the suprastructure are furnished with consecutive markings, in the longitudinal direction, so that they can be used, for example by means of an X-ray picture, as template when drilling the bone cavity.

To improve retention in the case of the EDH according to the invention, the endostructure is provided with undercuts and/or grooves and/or perforations and/or slight depressions and/or with a porous surface layer. This structuring of the surface can be carried out in any familiar way. In addition, the EDH can consist of any material exhibiting an adequate rigidity, so long as this is tolerated by the tissues or else is coated with another material being tolerated by the tissues. A particularly good retention is obtained with the porous surface layer, which, as dental periosteum substitute, guarantees an optimal growing together of bone and implant. The chances of the implant not being pushed out are hereby improved.

A porous surface layer for implants is exemplified in the DT-OS No. 2 419 080. One obtains this surface layer by adding incinerated bone- or dentine dust to a ceramic substance at 800° C.; on burning the ceramic bulk at a temperature of about 1000° C. the dust give off carbon dioxide, so that pores are formed whose individual diameters are on the average at least 100 $\mu$m.

An optimal retention of the EDHs according to the invention is obtained however if this is provided with a porous surface layer as is described in the patent application: Ser. No. 778,284.

In the case of the EDH according to the invention the porous surface layer covers the entire endostructure to the extrusion of same from the jaw ridge. The EDH is preferably covered with a glazing in the upward-bordering area, so that the part extending through the mucous membrane tissue exhibits a surface being as smooth as possible, on which no bacteria can set in.

Further advantages and details of the invention become evident from the accompanying drawings of preferred embodiments:

FIGS. 6–8 are concerned with an arrangement of two cutters, FIGS. 9–12 with an arrangement of three cutters.

Figure 13:
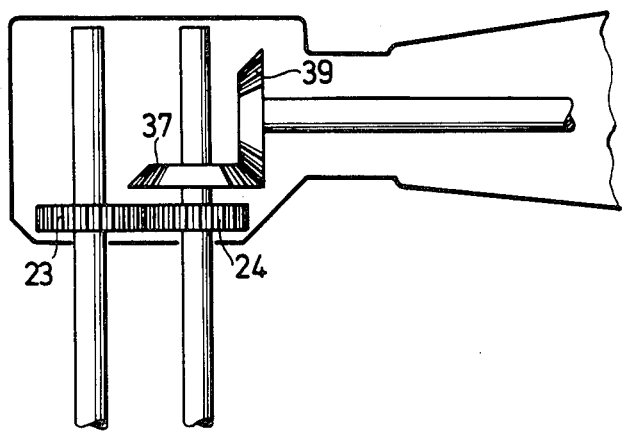
Figure 14:
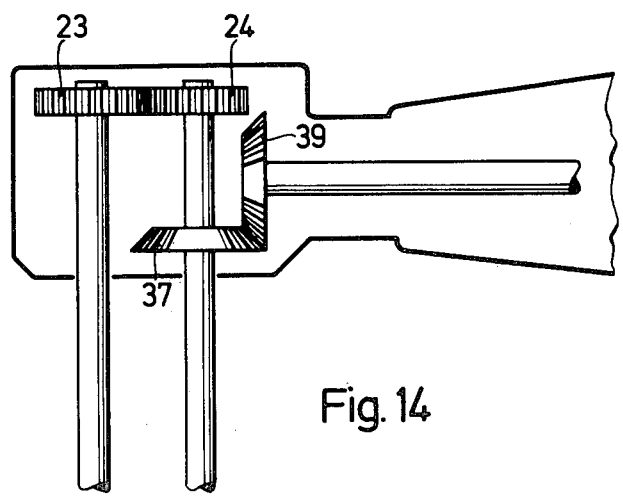
Figure 17:
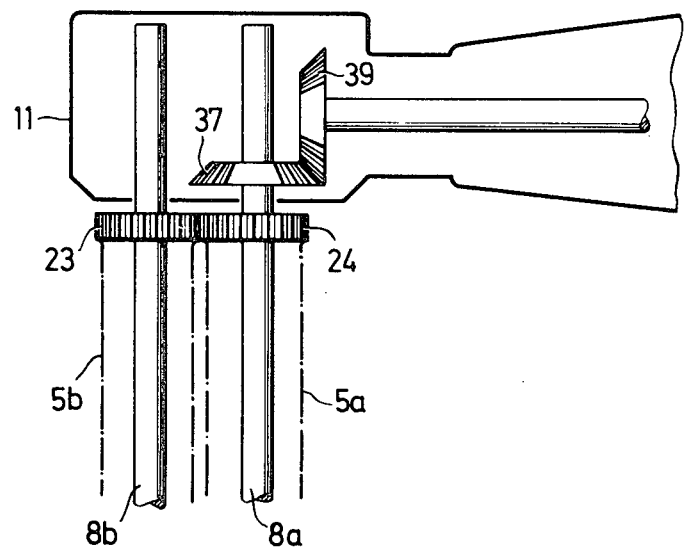
Figure 18:
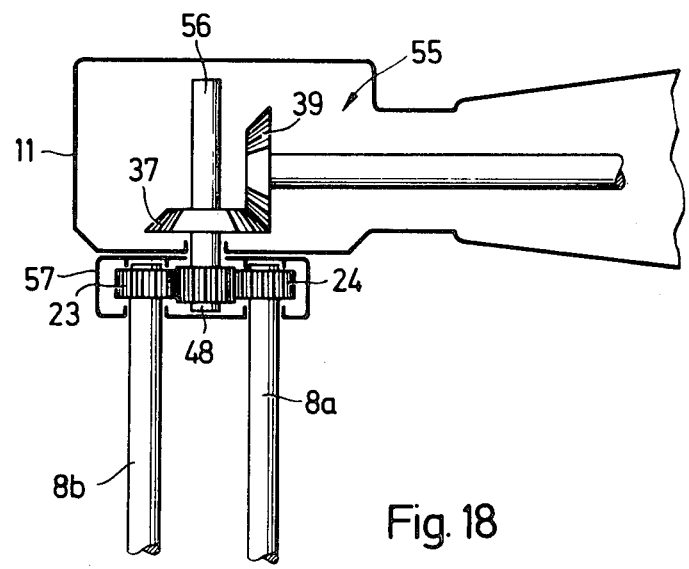

FIGS. 13–18 show variants of the drill head according to the invention, whereby in each case a shaft supported in the drill head is turned by a spur gearing; the gear unit connecting the cutters is formed in FIG. 13 from a spur gearing arranged at the bottom of the head casing, in FIG. 14 from a spur gearing arranged at the top of the head casing, in FIG. 15 by a chain-driven three-element spur gear system arranged at the bottom of the head casing, in FIG. 16 from a centrally-driven three-element spur gear system arranged at the bottom of the head casing, in FIG. 17 from an external spur gearing mounted as a unit on the drill head with the cutters and in FIG. 18 from an adapter gearing attachment mounted on a conventional drill head.

Figure 19:
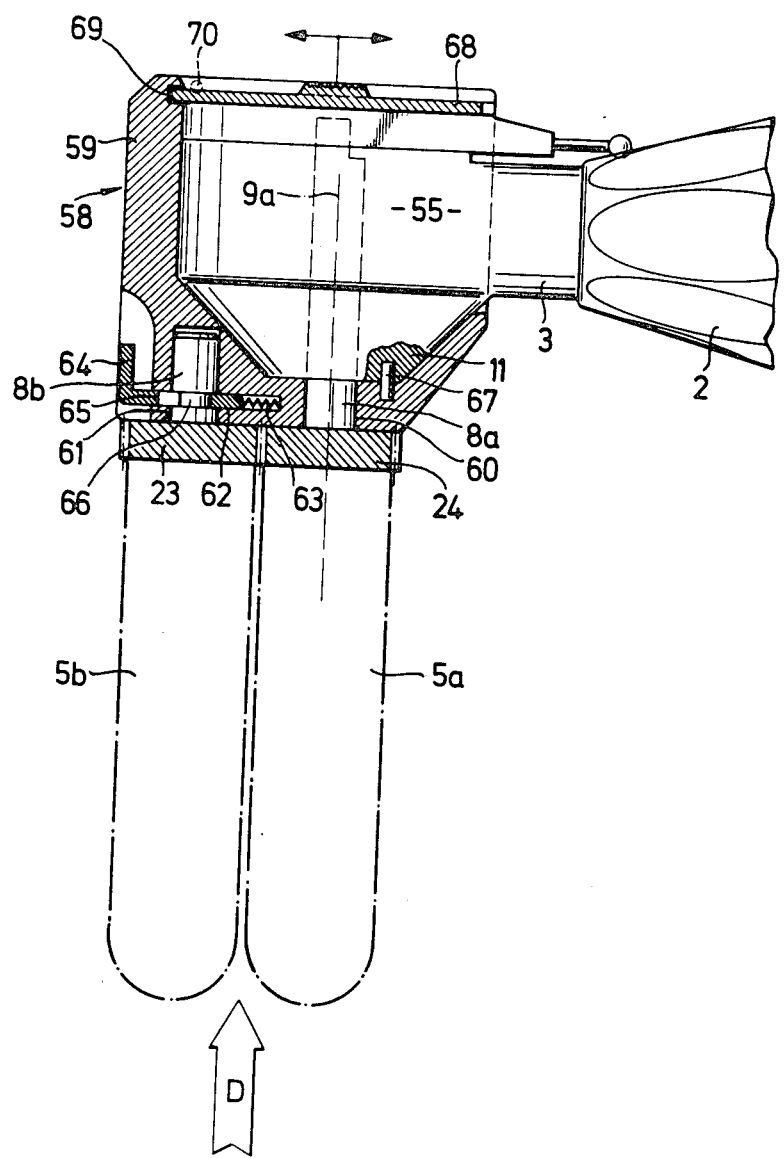

FIG. 19 shows, partly in section, an adapter attached to a conventional drill head.

FIG. 20 shows a further embodiment of an adapter for adapting a conventional drill head, in which case the adapter is fixed by means of a forked arm attaching to the neck of the conventional drill head—in FIG. 20a a longitudinal section through the adapter and in FIG. 20b a partly cut lateral view along the line XX—XX of the forked arm of the adapter. FIGS. 20c and 20d show two sectional views of shanks as used in the case of the cutters which are preferably used with the drill head according to the invention.

Figure 21A:
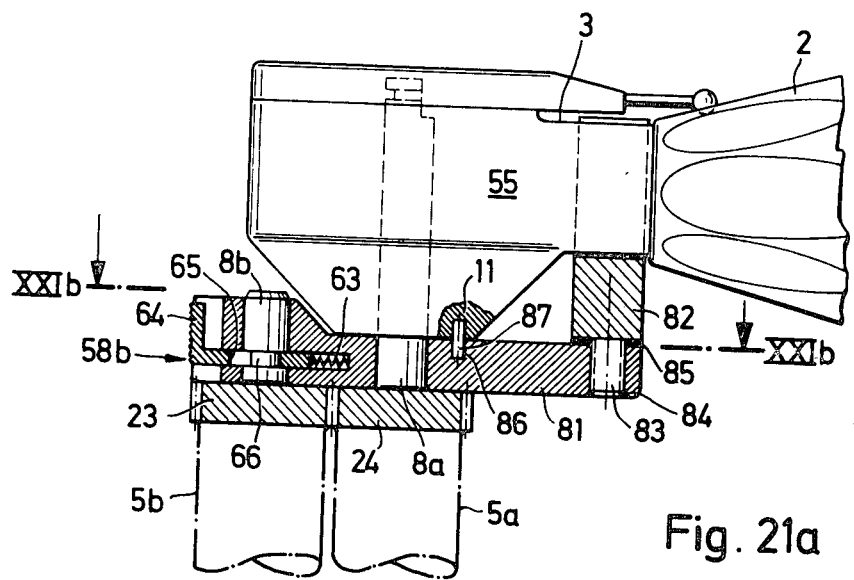
Figure 21B:
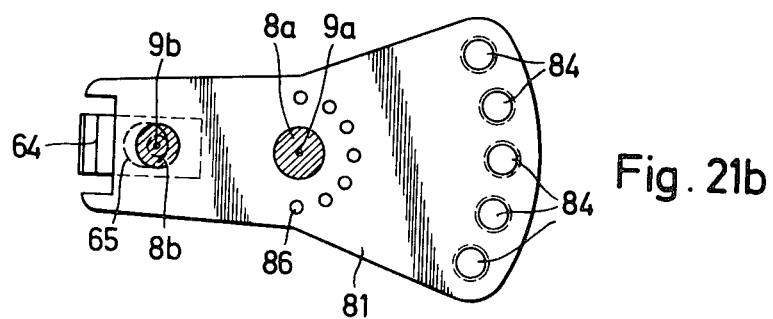

FIG. 21 shows a further version of an adapter for adapting a conventional drill head, whereby FIG. 21a shows a longitudinal section and FIG. 21b a top view of a swingable plate of the adapter shown in FIG. 21a along the line XXIII—XXIII.

FIG. 22 shows in a lateral view a first version of the bone drill according to the invention.

FIGS. 23–31 show cross sections through the cutting head of different variants of the bone drill shown in FIG. 22.

FIG. 32 shows a partly broken lateral view of a further variant of this bone drill.

FIG. 33a shows, in a partly cut lateral view and on an enlarged scale, a further variant of the bone drill, whereby the upper region of the cutting head is constructed as a perforated cogwheel.

FIG. 33b shows, for the clarification of the over-lapping cutting regions, a section along the line XX—XX from FIG. 19 as well as a section through a further identical bone drill lying directly behind and not being evident from FIG. 19.

FIG. 34 shows in a perspective, partly broken representation, a further version of the bone drill according to the invention.

FIG. 35 shows a section along the line XXXV—XXXV from FIG. 34.

FIG. 36 shows a section, corresponding to FIG. 35, through a symmetrical variant of the bone drill shown in FIG. 34.

FIGS. 37 and 38 show partial views, in perspective, of further variants of the bone drill shown in FIG. 34.

Figure 39:
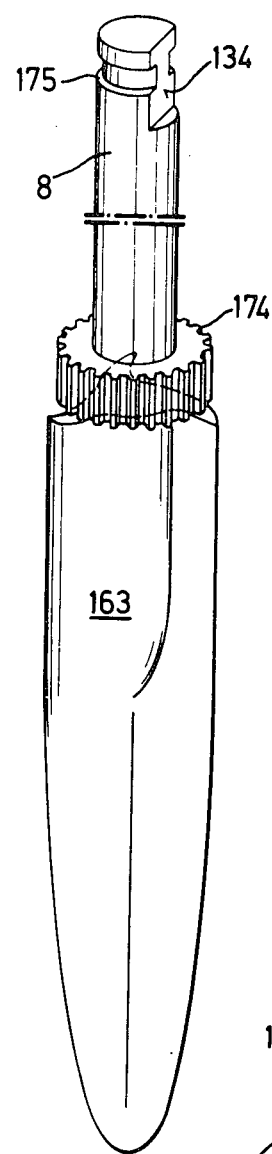

FIG. 39 shows, in perspective, a modification of the bone drill shown in FIG. 34, in which case the drill shank is provided with a cogwheel above the cutting head.

Figure 40:
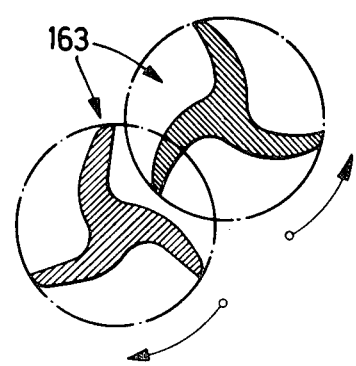

FIG. 40 shows in section the meshing of a clockwise and an anti-clockwise-rotating bone drill, corresponding to FIG. 34, but having however, drill shafts of thinner construction.

FIG. 41 shows a third version of the bone drill according to the invention, in a perspective, spread-apart presentation.

FIG. 42 shows a section along the line XLI—XLI of FIG. 41.

FIG. 43 shows a variation of the region represented in FIG. 42, of a bone drill according to FIG. 41.

FIG. 44 shows in section a partial area of a further variant of the bone drill shown in FIG. 41.

FIG. 45 shows in straightened-out form the area shown in FIG. 44.

FIG. 46 shows a section along the line XLVI—XLVI from FIG. 41.

FIG. 47 and FIG. 48 show in section detailed representations of anchorage variants of the cutting head with the drill shank, for the bone drill shown in FIG. 41.

Figure 49:
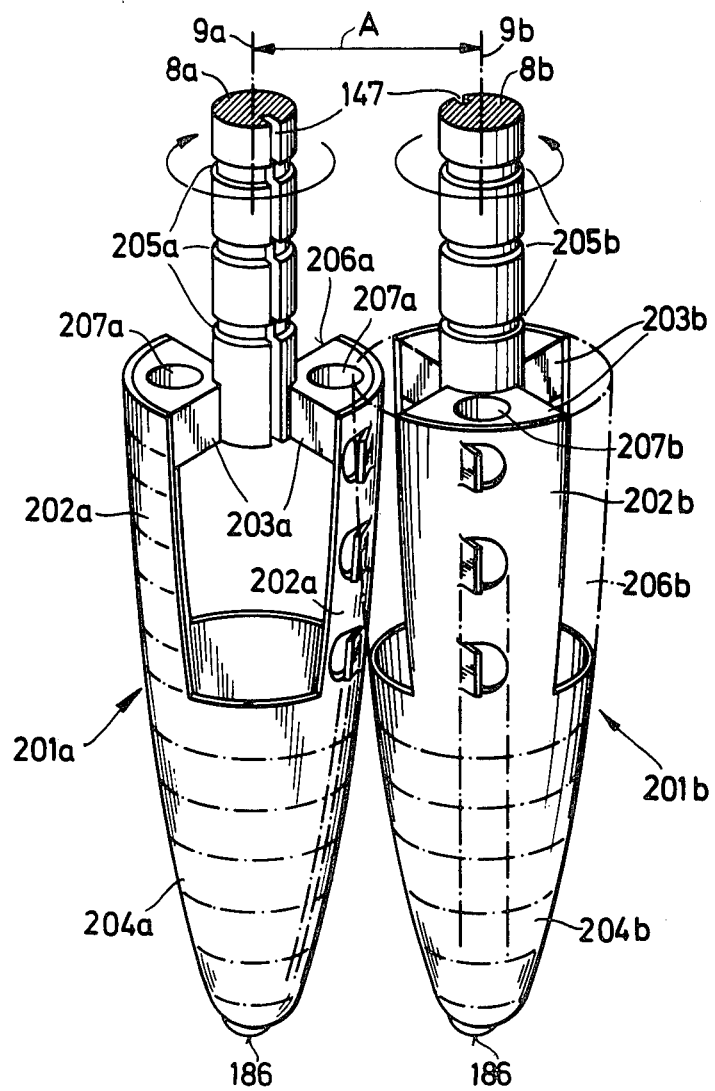

FIG. 49 shows in perspective view two bone drills according to the invention, overlapping with each other in operation according to a variant of the version shown in FIG. 41.

FIG. 50 shows in lateral view a first version of the enossal dental half-implant according to the invention, in which case the endostructure comprises two cone-like regions partly overlapping in the upper areas.

FIG. 51 shows a top view of the arrangement shown in FIG. 50, in the direction of the arrow LI.

FIG. 52 shows a lateral view of a further version of the enossal dental half-implant according to the invention, in which case the endostructure comprises three serially arranged cone-like regions, intersecting at the top.

FIG. 53 shows a top view of the enossal dental half-implant shown in FIG. 52, in the direction of the arrow LIII, which shows that the three cone-like regions are arranged along a slight curve.

FIG. 54 shows a top view of a further version of the enossal dental half-implant according to the invention, the three cone-like regions being arranged as a triangle in this case.

Figure 55:
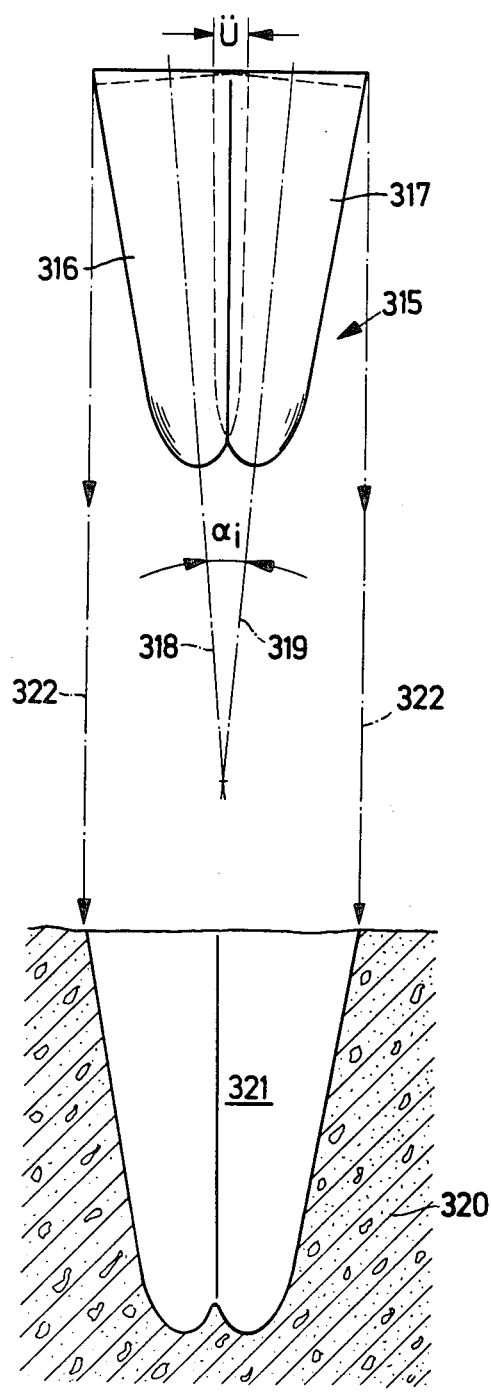

FIG. 55 shows in the upper part, in lateral view, a variant of the enossal dental half-implant according to the invention and shown in FIG. 50, whereby the cone-like regions are so inclined to one another that they overlap for most of their length, and in the lower part a schematic section through a bone cavity provided in a jaw ridge for the insertion of this implant.

Figure 56:
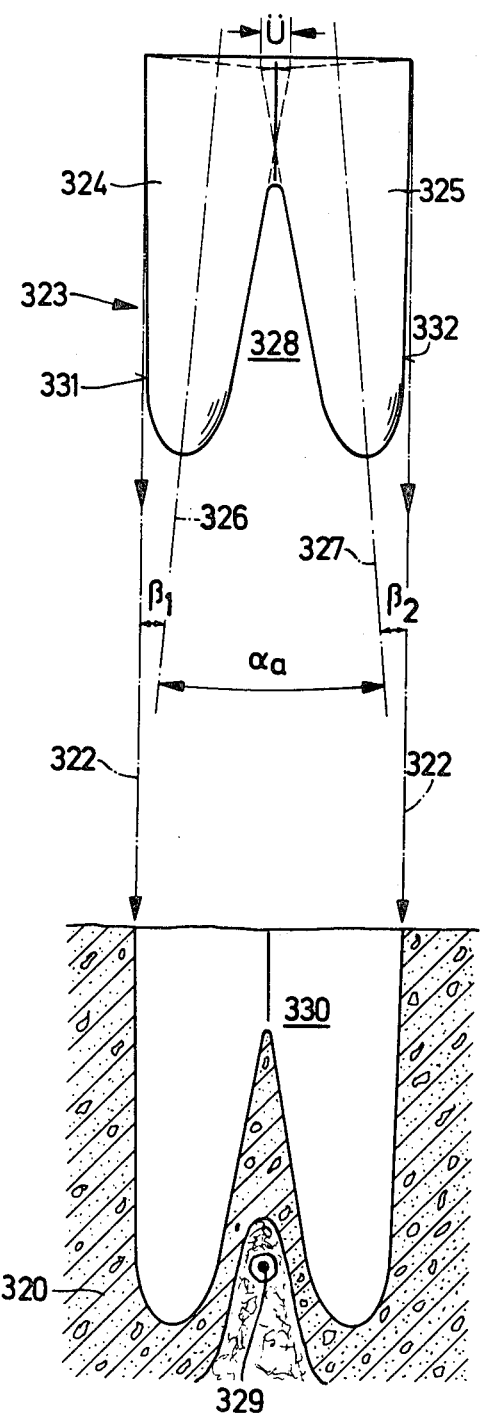

FIG. 56 shows in the upper region, in lateral view, a further variant of the enossal dental half-implant shown in FIG. 50, whereby the two cone-like regions are so inclined to one another that their outer edges run almost parallel to one another, meaning that a large V-shaped recess is created between them, and in the lower part a schematic section through a bone cavity provided in a jaw ridge for the insertion of this implant.

Figure 59:
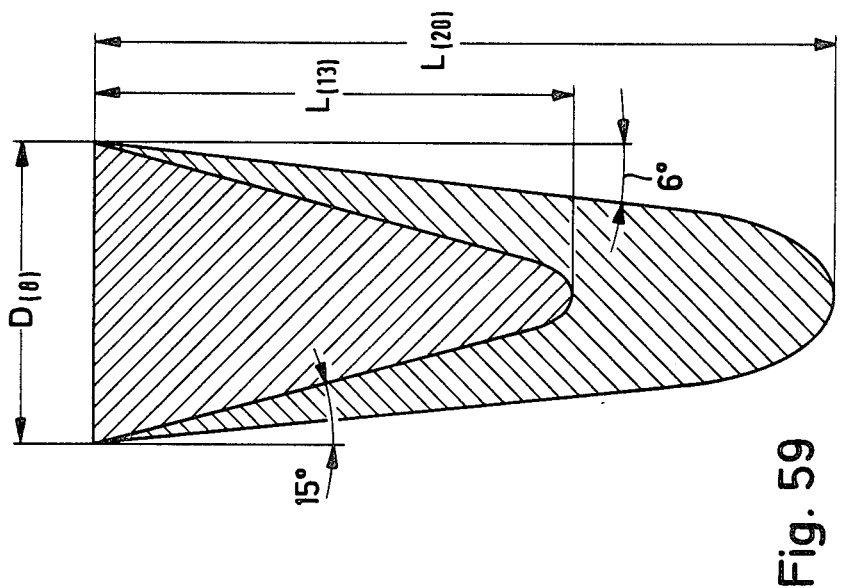
Figure 58:
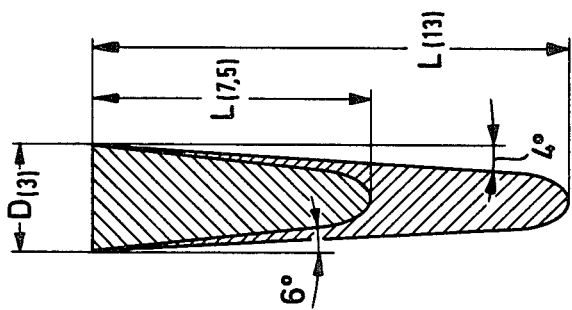
Figure 57:
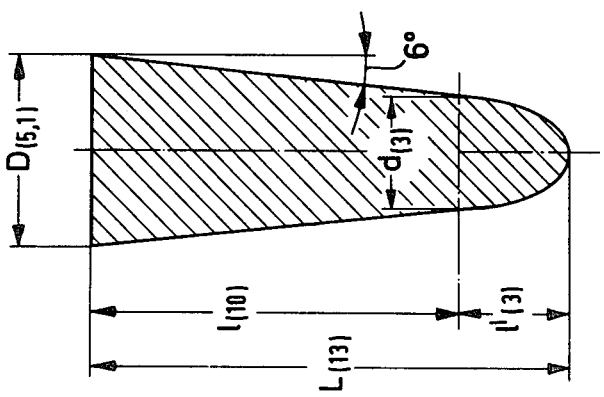

The FIGS. 57-59 show longitudinal sections along the line LVII—LVII from FIG. 51 through various versions of the cone-like regions composing the endostructure.

FIGS. 60-63 show in a perspective presentation various versions of the enossal dental half-implant according to the invention for clarification of some possibilities for attachment of the tooth superstructure to be attached onto the endostructure.

Figure 64:
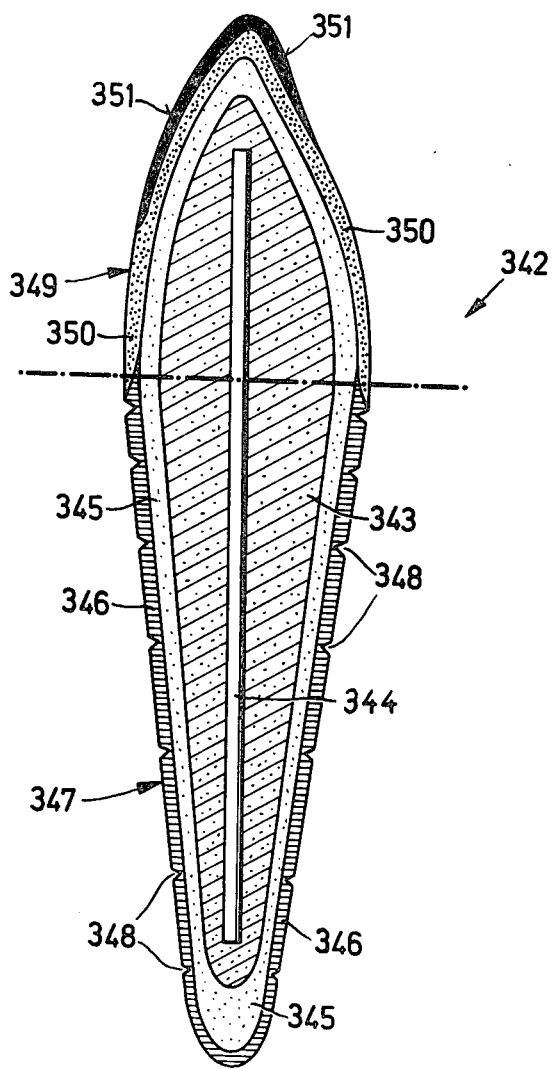

FIG. 64 shows a longitudinal section through one of the cone-like regions of the endostructure of an enossal dental half-implant according to the invention, with uniformly constructed exostructure which for example's sake is shown as an inciser crown.

Figure 1:
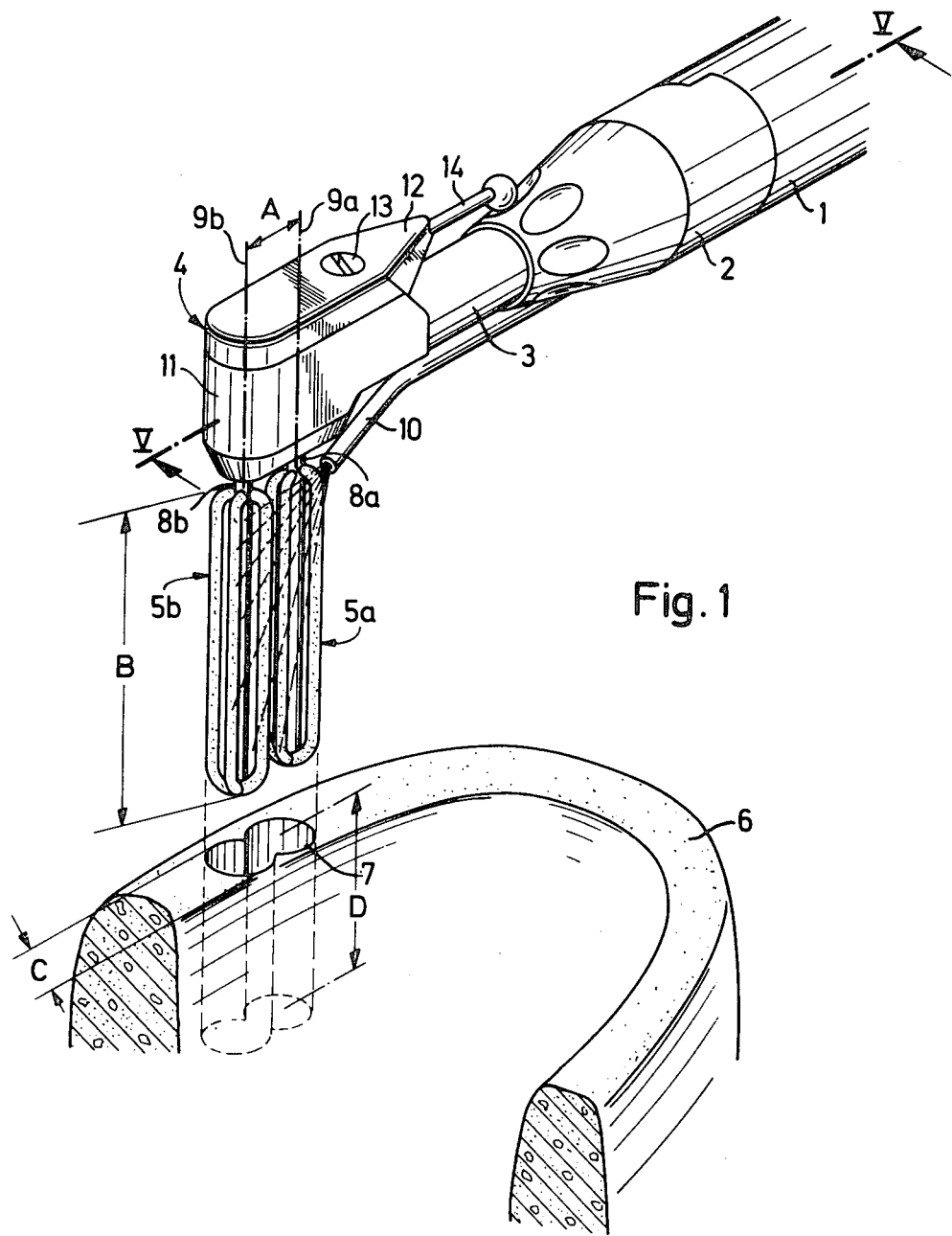
FIG. 1 shows in a perspective view an embodiment of the drill head according to the invention with milling cutters or respectively bone drills according to the invention lying one behind the other, and a cavity consisting of two overlapping cylindrical drill holes produced by the drills in a schematically represented jaw ridge.

In the drawings, equivalent parts or parts having an equivalent function are designated by the same reference symbols:

FIG. 1 shows, in a perspective presentation, a drill head 4 attached by its neck 3 via an intermediate piece 2 to a grip sleeve 1, the drill head being provided with cutters 5a and 5b lying one behind the other in the direction of the longitudinal axis V—V of the drill head. Underneath the cutters 5a and 5b a bone cavity 7, being formed by the cutters 5a and 5b and exhibiting a "dumb-bell-like" cross section, is shown in a schematically depicted jaw ridge 6. This configuration of the bone cavity shows that the shanks 8a and 8b of the cutters 5a and 5b are supported in the drill head in such a way that the distance A between their rotational axes 9a and 9b is smaller than the sum of the radii of the individual cutters. This is possible due to the special construction of the cutters, these consisting of a series of discrete, material-removing elements being distributed over the extent of the cutters and which in their entirety render the cutters as basket-like structures. The cutters 5a and 5b are mounted in the drill head 4 in such a way that they mesh with each other during contra-rotation. The material-removing elements consist in the case shown of rods, whose surfaces have been studded with diamond—i.e. coated with coarse diamond dust. This open construction of the cutters, making it possible for an overlapping in the area of cut, prevents clogging of the cutters and enables good dissipation of heat from the working area. In addition it enables the simple introduction of a rinsing- and cooling medium which is delivered from a nozzle 10, as schematically depicted by the broken line, in the region of the cutters. Naturally the drill head according to the invention can also be used with cutters where the sum of the maximal radii is less or equal to the distance A between the rotational axes. Such cutters with small diameters are used preferably for rough-drilling, in which case the separate drilling canals formed by them serve as guide for a subsequent drilling, eg. by means of the cutters 5a and 5b as shown in FIG. 1. Any shifting of the cutters is thus prevented. The cutters 5a and 5b shown in FIG. 1 produce bone cavities with straight cylindrical side walls, due to the outer edges of their cutting heads running parallel to the shanks over almost the whole length. For implants particularly in the dental field however, a downwardly-tapering contour of the cutter is generally preferred, as is shown for example in FIG. 20a.

The drill head 4 consists of a head casing 11, this being closed on the top side by a cover 12. The cover 12 can be deviated around a screw 13 as rotational axis, in order either to hold or to release the shanks 8a and 8b of the cutters. The cover 12 is rotated by means of a bolt handle 14 snapping shut in a bead of the intermediate part 2.

Figure 2:
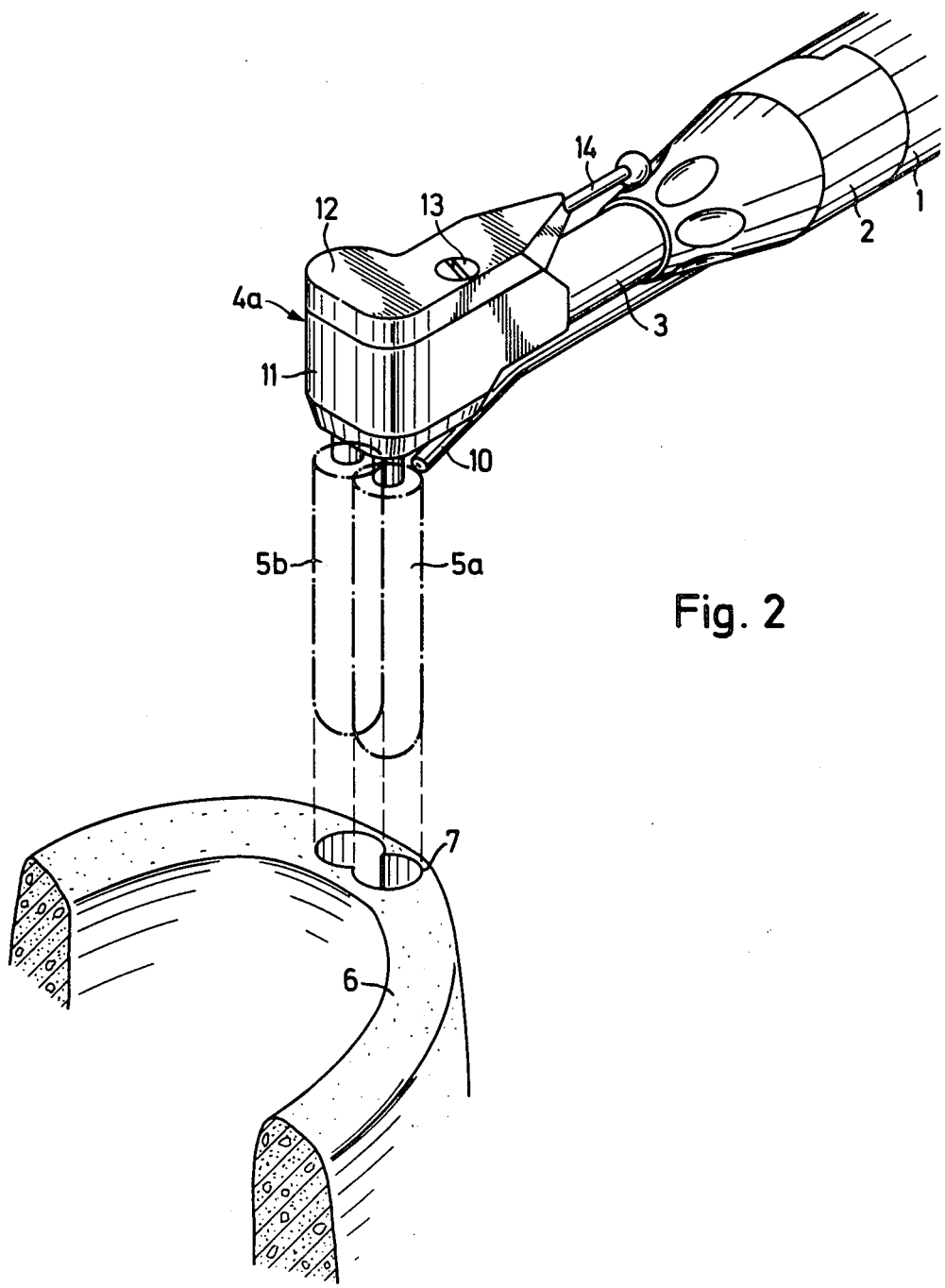
FIG. 2 shows a corresponding perspective view of a further embodiment of the drill head according to the invention with two cutters positioned beside each other.

The version shown in FIG. 2 differs from that of FIG. 1 only in that the cutters 5a and 5b lie next to one another and are supported transverse to the longitudinal axis of a corresponding drill head, this construction facilitating the production of a bone cavity 7 in the inciser teeth region of the jaw. The shanks of the cutters run parallel to one another (as also in the other version).

Figure 3:
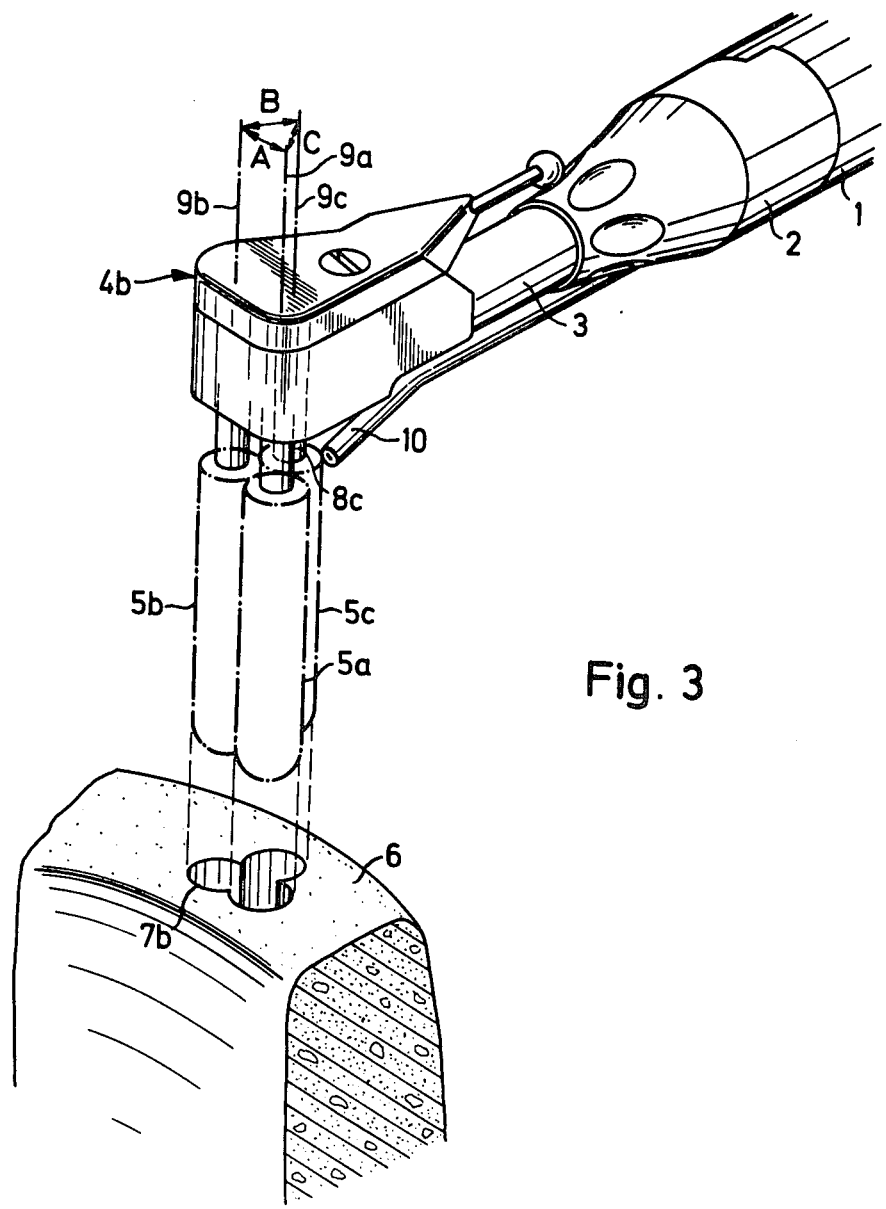
FIG. 3 shows a corresponding perspective view of a further embodiment of the drill head according to the invention, whereby the drill head is furnished with three cutters, whose rotational axes form the corners of a triangle.

FIG. 3 shows a drill head 4b corresponding to that of FIGS. 1 and 2 but having, in contrast to the previously-described examples, three cutters, 5a, 5b and 5c supported on its underside, whose rotational axes pass through the corners of a triangle. Thus when using cutters overlapping with one another a bone cavity 7b is created, with a clover-leaf cross section. The drill head 4b shown in FIG. 3 is equally suitable for a preparation in the rear jaw.

Figure 4:
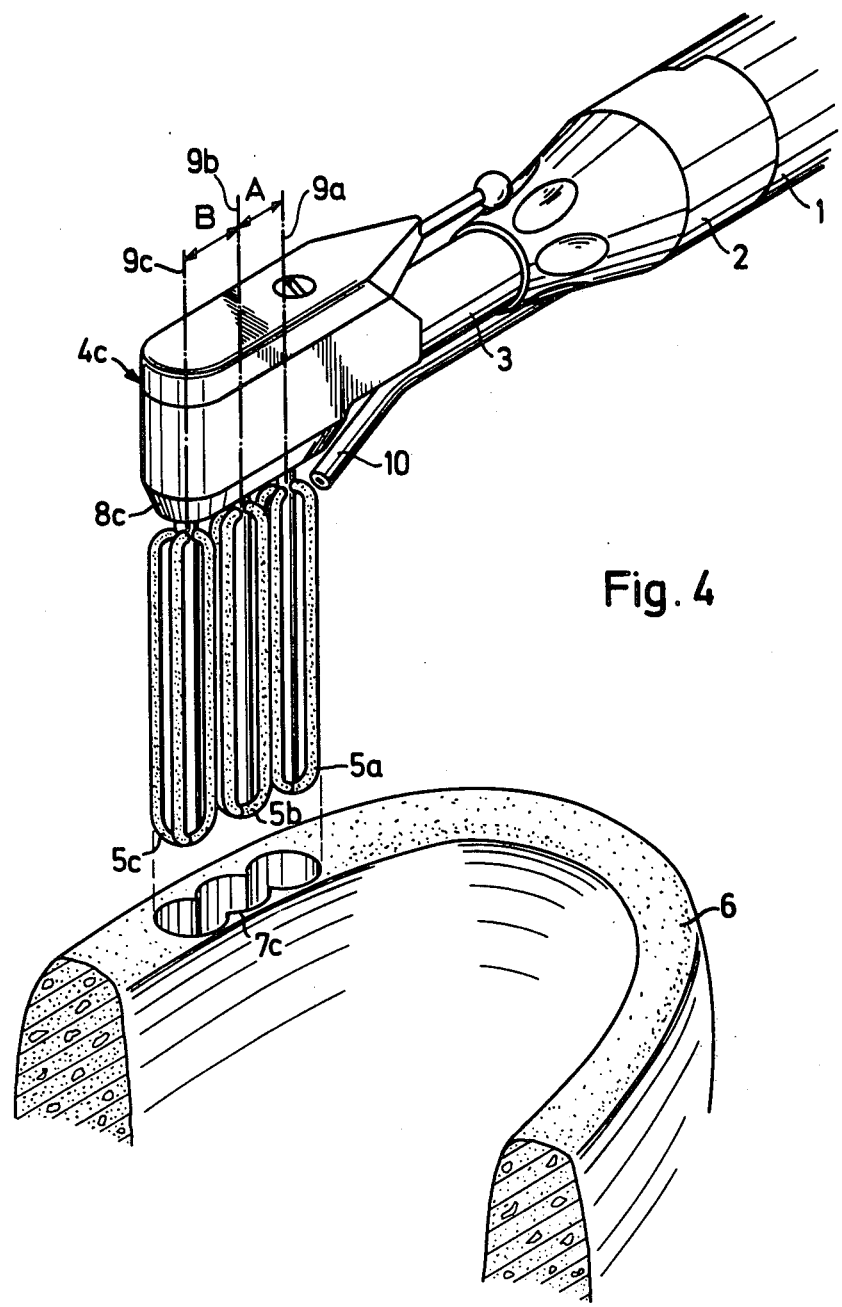
FIG. 4 shows a corresponding perspective view of a further embodiment of the drill head according to the invention with three cutters lying consecutively behind each other.

FIG. 4 shows in a corresponding presentation a drill head 4c, which holds three cutters 5a, 5b, and 5c in a row, in the longitudinal direction of the drill head. Using these cutters a slot-like bone cavity 7c provided with lateral constrictions can be made, being especially suitable for the insertion of leaf-like implants. In principle it is also possible to furnish the drill head with a mounting able to accommodate still further cutters, although such a construction is limited to special cases of application. Neither need the drill heads be driven in each case with the maximum numbers of cutters which they can accommodate.

The distances A, B and C between the individual rotational axes 9a, 9b and 9c can be constant or, as later more clearly explained, particularly by means of FIG. 8, they can be variable, in which case, as regards to size, they lie in a region of about 2.5 mm to about 10 mm, preferably about 2.8 mm to about 6 mm, if the drill head is used in the dental region.

FIG. 5 shows the example of drill head where all the elements of the mounting for the cutters, and for the driving mechanism, are attached in the interior of the head casing 11. The drill head is provided with a mounting for two cutters 5a and 5b lying one behind the other in longitudinal direction, and thus corresponds approximately to the version shown in FIG. 1.

Figure 5A:
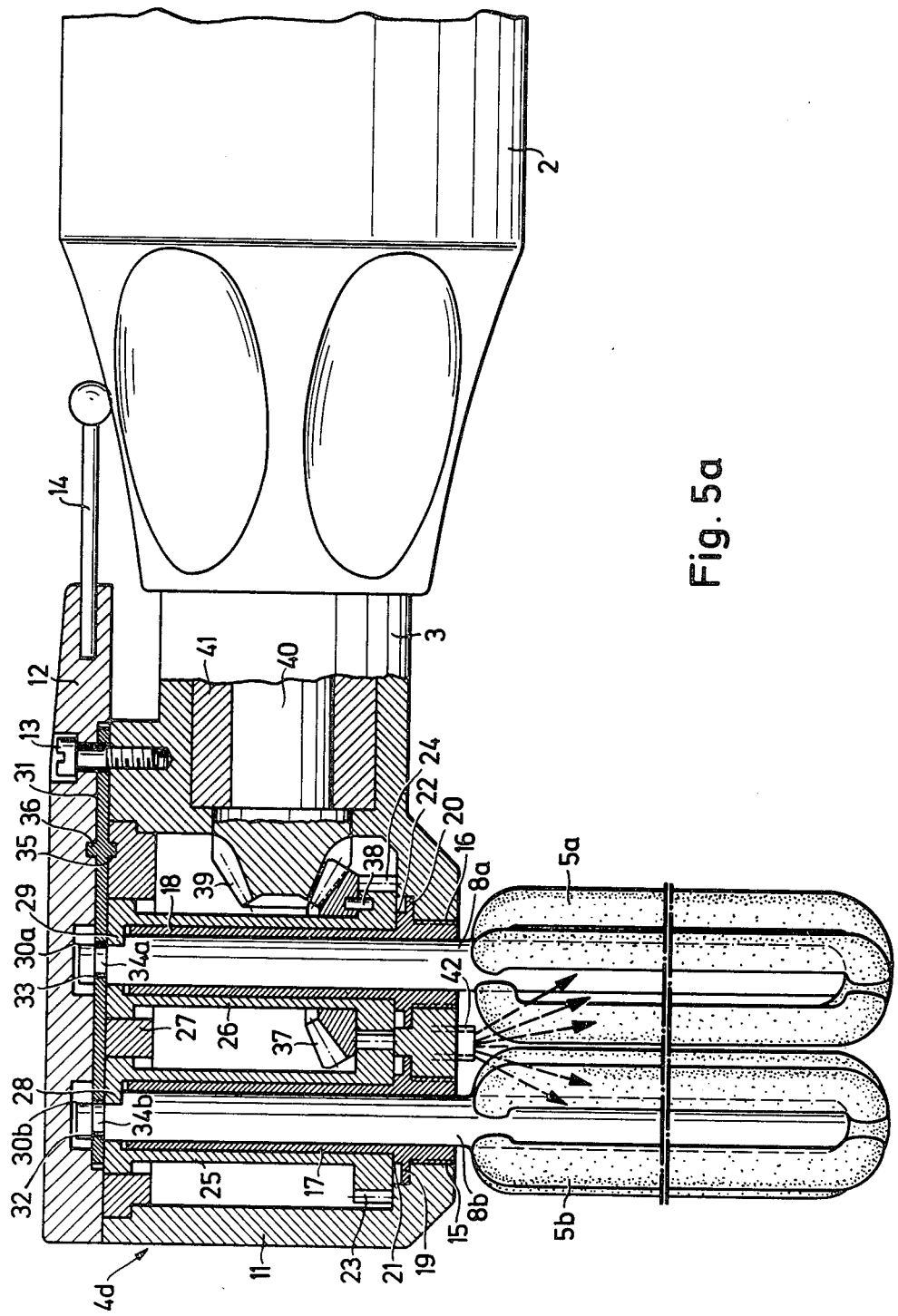
FIG. 5 shows the construction, partly broken open and partly in section, of the drill head according to the invention, where in FIG. 5a a force-locking drive and in FIG. 5b a form-locking drive for the cutters is depicted.

In the drill head 4d, shown in FIG. 5a, the head casing 11, extending downwards from the neck 3, is provided with two parallel tap holes 15 and 16 penetrating the floor region and into which tube-like bushings 17 and 18 are screwed from above until they adjoin the collars 19 and 20 in a groove of the head casing's floor region. The bushings are in addition provided on their outer side with collar-like projections 21 and 22, these serving as a support for the spur wheels 23 and 24 which engage with each other and form a gear system in the lower region of the head casing 11, this gear system connecting the cutters 5a and 5b in a freely-rotating manner. The spur wheels 23 and 24 are connected in one piece with axle-tube-like sleeves 25 and 26, which extend to the upper edge of the head casing 11. The upper ends of the axle-tube-like sleeves 25 and 26 are guided over reinforced regions in sleeve bearings, these being formed by bores of an inner cover 27 which is so inserted in the head casing that it is in alignment with the upper edge of the casing. The axle-tube-like sleeves 25 and 26 have at their upper ends inwardly projecting attachments 28 and 29, which engage with recesses or ground-down areas at the ends of the shanks 8a and 8b and thus drive same. The tube-like bushings 17 and 18 extend upwards in the interior of the axle-tube-like sleeves 25 and 26 to just under the projections 28 and 29 and guide these over their entire length. Their internal diameter is chosen such that they form a bush for the shanks 8a and 8b of the cutters.

The cutters 5a and 5b are mounted on the drill head 4d by means of a drill mounting cover 31, containg two hook-like recesses 32 and 33 open to one side, which, as in the position of the drill mounting cover 31 shown in FIG. 5a, engage with annular tee-slots 34a and 34b at the upper ends of the shanks 8a and 8b, so holding these in position. The drill mounting cover 31 is provided with a downward projection 35 which can be displaced to a certain angle in a corresponding circular groove in the surface of the inner cover 27. The drill mounting cover is connected to the cover 12 by a further upward projection 36 which projects into a corresponding recess in the cover 12, so that it can be so far displaced by rotating the cover 12 around the screw 13 that the shanks 8a and 8b come out of the hook-like recesses 30a and 30b and can be pulled downwards out of the drill head 4d.

In the example shown in FIG. 5a the cover 12 has blind-hole recesses in the area of the cutters' rotational axes, into which the upper ends of the shanks 8a and 8b project.

These recesses reach through the cover 12 if cutters are to be used whose shanks are provided with several annular tee-slots being arranged along the rotational axis at intervals. These annular tee-slots correspond in each case to the annular tee-slots 34a and 34b. Thus when there are two cutters held in the drill head, the one can be pushed further into the drill head than the other. The lower ends of the cutters are in this case of varying distance under the drill head. In this way "dumbbell-like" bone cavities being of varying depth in different regions can be made.

In the case of a drill head for two cutters it is in principle sufficient if only one cutter is adjustable.

The drill head is driven in the usual manner by means of a bevel gearing. The bevel gearing contains a bevel pinion 37 inserted on the axle-tube-like sleeve 26, the bevel pinion being connected in a freely-rotating manner with the sleeve via a pin 38. A pinion 39 mates with the bevel pinion 37, the pinion 39 being positioned on the front end of the driving shaft 40 and being inserted into the drill head from the right with a sliding bearing 41 not visible in the drawing.

At the bottom of the head casing 11, between the tap holes 15 and 16, there is a nozzle 42 attached, which is supplied with a cooling medium by a lead not shown in further detail in the interior of the drill head. The nozzle 42 delivers the cooling medium to the region between the cutters 5a and 5b and in the interior of the cutters so that good rinsing and cooling is achieved.

The spur wheels 23 and 24, the upper ends of the axle-tube-like sleeves 25 and 26, as well as the shanks 8a and 8b where they enter the head casing 11, can also be mounted by means of ball bearings instead of sliding bearings as in the case shown.

The drill head shown in FIG. 5a is assembled as follows: first of all the tube-like bushings 17 and 18 are screwed tight from above into the head casing 11, whose covers 12 and 27 have been removed, until their collars 19 and 20 lie on the floor of the head casing 11a. Subsequently the spur wheels 23 and 24 are pushed from above over the tube-like bushings 17 and 18, the bevel pinion 37 being already connected to the spur wheel 24. In so doing care must be taken that the attachments 28 and 29 assume such angular positions that the cutters 5a and 5b to be inserted can interlock. Then the pinion 39, being connected with the shaft 40, and the inner cover 27 are positioned in arbitrary sequence. After putting on the drill mounting cover 31 and the cover 12, the screw 13 is screwed tight, thus completing the assembly of the drill head. The shanks 8a and 8b of the cutters 5a and 5b, which are subsequently introduced into the tube-like bushings 17 and 18 are held in the drill head by rotating of the cover 12 and of the drill mounting cover 31 connected to this. The cutters 5a and 5b can now be driven contra-rotating through a rotation of the pinion 39 via the bevel pinion 37 and the gear system comprising the spur wheels 23 and 24.

Figure 5B:
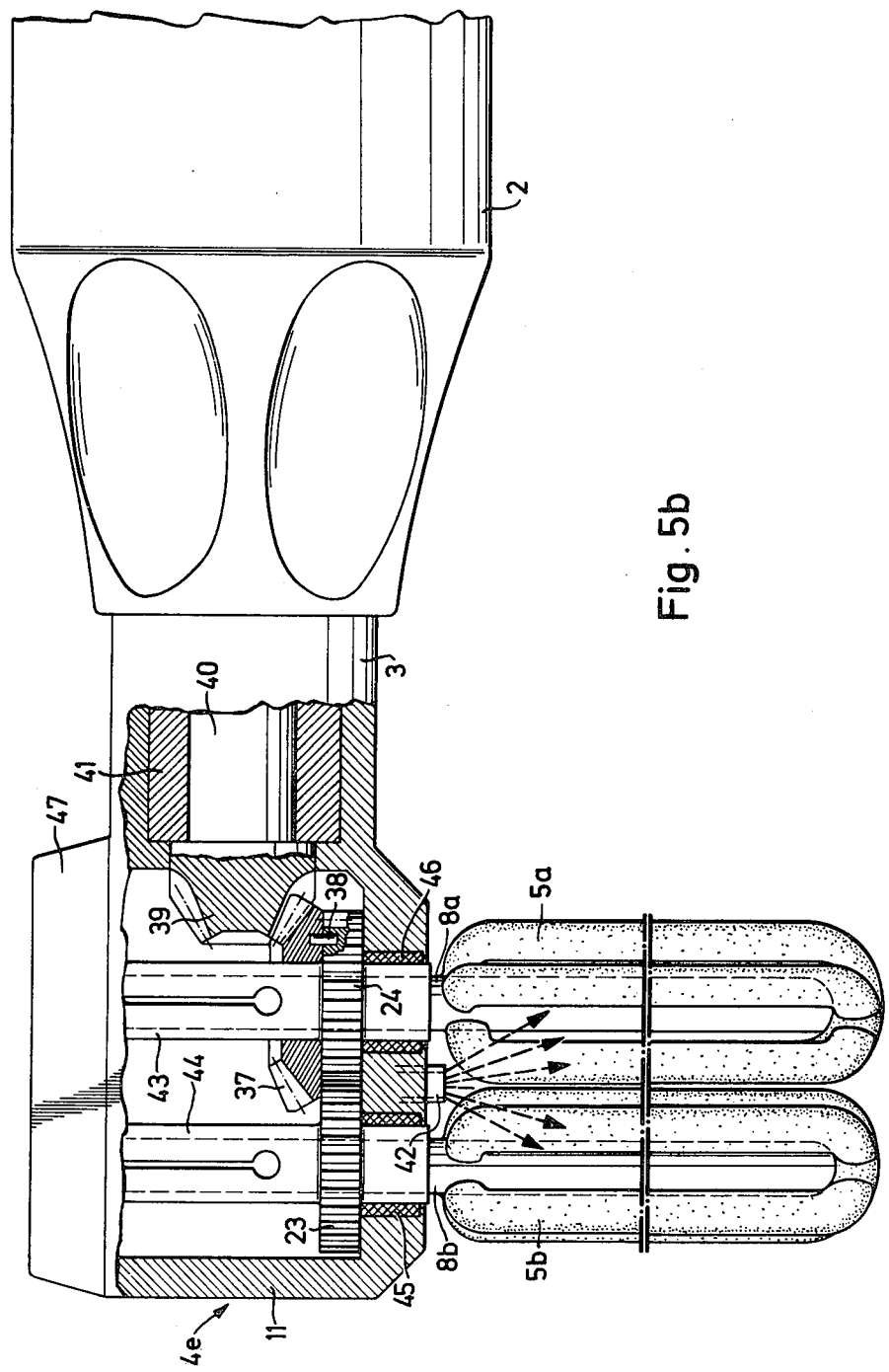

In the version of the drill head shown in FIG. 5b the shanks 8a and 8b of the cutters are lodged in a force-locking manner by adapter sleeves 43 and 44, these being guided in bearings 45 and 46 at the bottom of the head casing 11 as well as sometimes in corresponding bearings not shown in more detail at the upper side of the head casing. The spur wheels are attached to the lower parts of the adapter sleeves 43 and 44, the spur wheels being driven by the bevel pinion 37 and the pinion 39 as in the example from FIG. 5a. The head casing 11 is in this case provided with a firm cover 47 which is removed only when assembling the drill head. When assembling this drill head the adapter sleeves 43 and 44, being provided with the cogwheels 23, 24 and 37, are introduced into the head casing from above and are held with their lower ends in the bearings 45 and 46. After putting on the cover and pushing in the pinion, the drill head is ready for operation.

In the following the gearing variants shown in FIGS. 6-12 which connect the cutters held in the drill head with one another so as to induce driving, should be more clearly explained. In the schematic presentation all circles with slanting shading designate the shanks of the rotating cutters, whose rotational axes pass through the middle of these circles. Solid black segments characterize the driven axes in each case. The points designated by crosses indicate the rotational axes of idler gears which effect a synchronous rotation of the cogwheels connected with them. The rotational directions of the cogwheels are shown by arrows.

Figure 6:
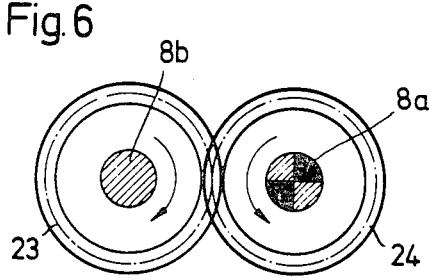
FIGS. 6–12 show in show in schematic presentation variants for the gear unit, which connects the cutters in a freely-rotating manner with each other.

The gear system shown in FIG. 6 corresponds to an arrangement as is realized in FIG. 5. Here the cogwheels 23 and 24 are moved contra-rotationally, the shank 8a being driven directly. In the case of the gear systems in FIG. 7, there is a driven idler gear 48 being connected with the cogwheels 23 and 24, so that these are driven in the same direction.

Figure 7:
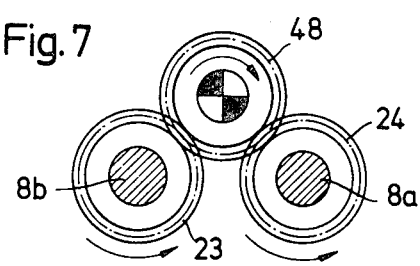
Figure 8:
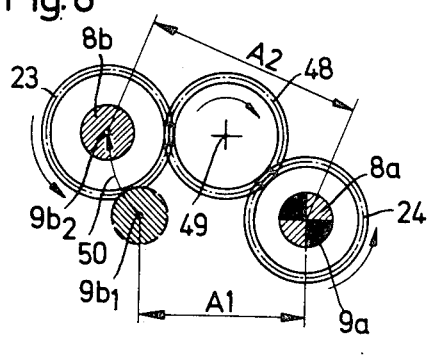

The gear system in FIG. 8 corresponds essentially to that of FIG. 7. In this case, however, the shank 8a drives the cogwheel 24 directly. The special feature of this gearing lies in that the rotational axis 9b for the shank 8b can be deviated around the rotational axis 49 of the idler gear 48 along a circular arc 50, so that it can, for example shift from the shaded position $9b_1$ to the position $9b_2$. The radius of the circular arc 50 corresponds to the sum of the radii of the cogwheels 23 and 48. Through this deviation the distance designated A between the rotational axes 9a, 9b is altered. In the case shown a deviation of the rotational axis $9b_1$ to $9b_2$ effects a change in distance of $A_1$ to $A_2$. When instead of the case shown in FIG. 8, where only one rotational axis is deviated, both rotational axes corresponding to the cogwheels 23 and 24 are deviated at the same time, as in the arrangement shown in FIG. 7 for example, then besides an alteration in distance between the rotational axes it is possible that the same orientation to their connecting lines be retained.

Figure 9:
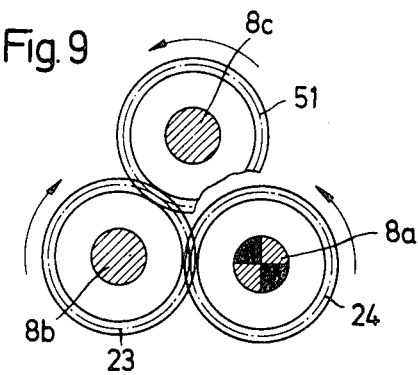

FIG. 9 shows the simplest arrangement of a gear system for driving three cutters. This arrangement is based on that of FIG. 6, whereby a further cogwheel 51, which drives the shank 8c of the cutter 5c, meshes with the cogwheel 23. The cogwheel 51 is here attached levelly displaced with respect to the cogwheel 24, so as not to interfere. Since the shank 8a is driven, the cogwheels 24, 23 and 51 are joined in a chain, so that the cogwheels 24 and 51 rotate synchronously whilst the cogwheel 23 rotates in opposition to them.

Figure 10:
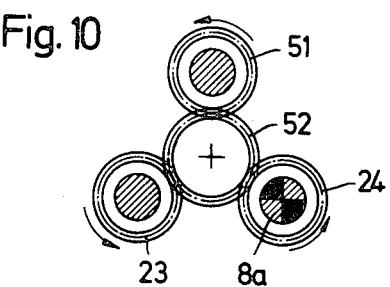

In order that the three cutters arranged in a triangle rotate in the same direction FIG. 10 shows a gear system with an idler gear 52 supplied, which meshes with the cogwheels 23, 24 and 51.

Figure 11:
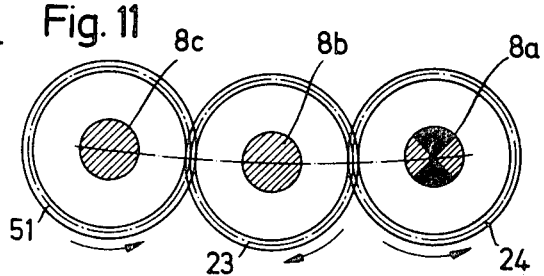

FIG. 11 shows a gear system suitable for the drill head of FIG. 4, whereby the individual cutters are arranged along a slight curve. Every two cogwheels engaging with each other, 23,24 or respectively 51,23, rotate in opposition.

Figure 12:
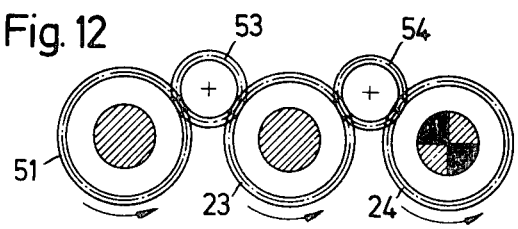

FIG. 12 shows finally a gear system whereby three cutters arranged serially are driven synchronously, this being achieved by having an idler gear 53, 54 between every two of the cogwheels shown in the arrangement of FIG. 11.

An alteration in the distance between the individual rotational axes can naturally be undertaken also in the versions of gear systems shown in FIGS. 10-12, by means of a corresponding deviation of individual cogwheels as explained for FIG. 8.

The FIGS. 13-18 show schematic longitudinal sections through different versions of the drill head according to the invention, whereby some possibilities of realizing the previously described driving schemes are shown. FIGS. 13 and 14 show the two-unit drive corresponding to FIG. 6, FIG. 13 as a spur gearing arranged under the bevel-gear drive arranged at the bottom of the head casing, FIG. 14 as a spur gearing arranged above the the bevel-gear drive in the upper region of the head casing. FIG. 15 shows an example for the three-unit drive shown in FIG. 9, whereby the spur gearing formed by the cogwheels 23, 24 and 51 is attached in the lower region of the head casing beneath the bevel-gear drive. FIG. 16 shows an example for the three-unit drive shown in FIG. 10, whereby in contrast to this however, the cogwheel 52 instead of the cogwheel 24 is turned by the bevel-gear drive.

The arrangement of FIG. 17 corresponds essentially to that of FIG. 13; in this case however the spur gearing formed by the cogwheels 23 and 24, which drives the shanks 8a and 8b contra-rotationally, is attached outside the head casing, the latter containing only the bevel-gear drive with the bevel pinion 37 and the pinion 39, and mounts for the shanks 8a and 8b. The cogwheels 23 and 24 are, as shown in the figure, connected with the shanks 8a and 8b and attached at the upper edge of the cutters 5a and 5b. The gearing, which connects the cutters in a freely-rotating manner with each other, is thus formed by the insertion of the cutters in this case.

FIG. 18 shows a further variant of a two-unit drive, where the head casing accommodates only the constructional elements of a conventional drill head 55—ie. the mounting for a shank 56 as well as the bevel-gear drive comprising the bevel pinion 37 and the pinion 39. The shank 56 accommodated by the conventional drill head 55 forms a driving connection to an adapter gear attachment 57, which contains in its interior a spur gearing corresponding to the arrangment in FIG. 7 whose cogwheels 23 and 24 turn the shanks 8a and 8b.

FIG. 19 shows an adapter 58 with which a conventional drill head 55 can be adapted for the simultaneous driving of several cutters.

The adapter 58 consists of a pot-like casing 59 which can be inserted from underneath into the head casing of the conventional drill head 55 in the direction of arrow D. The casing 59 contains a cutout in the region of the neck 3 of the conventional drill head 55, the neck 3 projecting out of this cutout as can be seen in the drawing. The inner contours of the casing 59 correspond essentially to the outer contours of the conventional drill head 55. In the floor region of the casing 59 there are two bore cylinders 60 and 61 positioned parallel to one another.

The bore cylinder 60, which reaches up through the casing 59, is so positioned in this that, when the adapter is inserted into the conventional drill head 55, it is in exact alignment with the bore cylinder of the conventional drill head 55, in which bore cylinder the shank 8a of a drill or a cutter is held force- or form-locked and driven. The second bore cylinder 61 extends as far up as possible in the adapter and guides the shank of the second cutter 5b. The bore cylinders 60 and 61 are constructed as bearings and guide the shanks 8a and 8b. The bore cylinder 61 is penetrated laterally by a canal 62 in which a sliding plug, being prestressed towards the outside by a spring 63, is introduced. The outer end of the sliding plug 64 extends beyond the edge of the adapter and is accommodated in a recess of the casing 59 in the case shown. It contains a continuous bore cylinder 65 whose diameter is larger or equal to the diameter of the bore cylinder 61. The bore cylinder 65 assumes such a postion with respect to the sliding plug 64 that the shank 8b, being provided with an annular tee-slot 66, of the cutter 5b can be pushed into the bore cylinder 61 when the sliding plug 64 is pushed inwards against the force of the spring 63. As soon as the shank 8b has assumed the desired position, the sliding plug 64 is released so that it is pushed outwards again by the spring 63. In so doing it engages in the annular tee-slot 66.

The adapter 58 is in addition provided with a pin 67 which locks in a borehole in the floor of the head casing 11, so preventing any twisting of the adapter 58 relative to the conventional drill head 55, should this be of rotational symmetric construction. In this case the adapter can also be rotated through discrete angles to the rotational axis 9 by making use of boreholes, not visible in the drawing, positioned adjacent to one another in a circle around the rotational axis 9a on the underside of the floor of the head casing 11 or respectively on the inner side of the floor casing 59, and a corresponding locking mechanism.

In addition the adapter 58 has a sliding cover 68 serving as anchoring element which can be pushed into a groove 69 of the casing 59 and which is supported on the top side of the conventional drill head 55. The drawer-like cover 68 locks releasably with a small recess or bead in a lateral lock 70.

The gear unit by means of which the rotation of the first cutter's shank 8a, being driven by the conventional drill head 55, is transferred to the shank 8b of the second cutter, is made up of two spur gears 23 and 24 meshing with each other and being attached on the underside of the shoe-like adapter 68, the rotational axes of the spur gears being in alignment with the rotational axes of the shanks 8a and 8b. The cogwheels 23 and 24 can be supported via suitable bearings on the underside of the casing 59, or, as shown in FIG. 19, be fixed to the shanks 8a and 8b of the cutters, so that they are inserted with these onto the adapter 58.

When the conventional drill head 55 is to be used with the adapter 58, the adapter cover 68 is pushed out from the groove 69 and the adapter then inserted from underneath in the direction of the arrow D, the pin 67 fitting into the corresponding borehole in the headcasing 11 and the casing 69. Subsequently the cover 68 is pushed back into the position shown in FIG. 19. After inserting the cutters 5a and 5b in the holes 60 and 61, the instrument is ready for operation, whereby the cutter 5a is driven by the conventional drill head 55 and via the cogwheels 23 and 24 the cutter 5b is also driven.

The versions shown in the FIGS. 20a-d show an adapter 58a on a conventional drill head 55. The adapter 58a consists of a base plate 71 being provided, in a way corresponding to the floor region of the casing 59 in the version shown in FIG. 19, with parallel-running bore cylinders 52 and 53 into which the shanks 8a and 8b of the cutters are inserted. The plate is provided on one side with a forked arm 74 standing almost vertically upwards, whose dovetailing free ends 75 and 76 encircle the neck 3 from underneath, as can be seen most clearly in FIG. 20b.

The inner contour of the forked ends correspond exactly to the outer contour of the neck 3. The free ends 75 and 76 of the forked arm 74 each carry a firing notch 77 resp. 78 on their inner sides. The firing notches consist, as exemplified in sectional view, of spring cages accommodated in holes in the free ends 75 and 76 and being prestressed by springs 79, the inwardly-projecting ends of the spring cages fitting against the upper regions of the neck 3.

The shanks 8a and 8b of the two cutters as well as their drive are mounted according to the example shown in FIG. 19, whereby in this case however the following cutter, 5b, not being directly driven, is attached rearwardly displaced with respect to the drill head 55, in the direction of the intermediate piece 2. This occurs for one because the adapter 58a, consisting of the base plate 71 and the forked arm 74, exhibits great rigidity in this region, and secondly to prevent the overall dimensions of the drill head, being furnished with the adapter, from becoming too large in view of the little working space available in the mouth of the patient.

In the arrangement shown in FIG. 20 the shanks 8a and 8b are additionally provided with at least one groove 80a or 80b, running along the entire length parallel to the axis of rotation. FIG. 20c shows the cross section of the shank 8a, which is furnished with such a longitudinal groove 80a. FIG. 20d shows a variation of the shank 8b, being provided with three grooves 80b radially arranged around the circumference. The grooves make it possible to insert the cogwheels 23 and 24 onto the shanks. In the case of the driven shank 8a they can serve further fo a form-locking drive of same in the conventional drill head 55.

When assembling the adapter 58a together with the conventional drill head 55 the forked arm 74 is positioned against the neck 3 and then pushed forcefully upwards, so that the firing notches 78 move outwards against the force of the spring 79 and the neck 3 comes to lie between the free ends 75 and 76 of the forked arm 74. The firing notches, returning to their starting position, hold it there firmly. The shank 3a is subsequently guided through the bore cylinder 72 of the base plate 71 and pushed into the chuck of the conventional drill head 55, the adapter being simultaneously centered. The shank 8b of the second cutter is subsequently pushed into the bore cylinder 73 and arrested there. The arrangement can now be put into operation, whereby the cogwheel 24 slipped onto the shaft 8a via the groove 80a drives the cogwheel 23, slipped onto the shaft 8b via the groove 80b, in a contra-rotating direction.

FIGS. 21a and 21b show a further variant of an adapter 58b on a conventional drill head 55. The adapter 58b consists of a swingable plate 81, in which the shanks 8a and 8b for the cutters are mounted, as in the versions exemplified in the the FIGS. 19 and 20. The plate 81 is similarly provided with a forked arm 82 standing up almost vertical to one of its ends and which, with its upper region engaging with the neck 3 of the conventional drill head 55, corresponds to the forked arm 74 in FIG. 20. In contrast to the adapter shown in FIG. 20 the mounting for the shank 8b is attached on the side of the plate facing away from the arm 82. The plate 81 is releasably connected with the arm 82 via a pin with thread 83, which projects from the underside of the arm 82 and is screwed into a taphole 84 of the plate 81. There is a damping element 85 positioned between the plate 81 and the arm 82, which consists of rubber or some other elastic material.

A further possibility for anchoring is to provide the underside of the arm 82 with a hole having an internal thread, into which a screw is releasably screwed from the underside of the plate through the bore cylinder 84.

FIG. 21b shows how the bore cylinders 84 in the plate 81 are arranged along a circular arc around the rotational axis 9a as center point. The plate 81 can thus be adjusted at different angles to the longitudinal axis of the drill head by having the pin 83 in the different holes. Concentric to the bore cylinders 84 the plate 81 has another series of discrete bore cylinders 86, in which a pin 87, being accommodated in the floor of the head casing 11 fits. The pin 87 serves to center the adapter 58b.

The bore cylinder 86 and the accompanying pin 87 can also be replaced by another adjusting device or completely left if the centering effected by the cutter shank 8a, introduced into the conventional drill head 85, is sufficient.

In the previous versions of the drill head or adapter the mounting for the shanks of the cutters is in general so constructed that the rotational axes of the cutters run parallel to one another. However, for a series of applications, whereby an optimal bifurcation of the root region of the bone cavity and the implants embedded is desirable, it can be advantageous if the mounting supports the shanks in such a way that the rotational axes of at least every two shanks intersect at a point lying above the lower edge of the drill head. Thus the points of the cutters lie further apart than do their bases. In the reverse manner a bifurcation being as small as possible of the bone cavities produced and of the implants embedded can be attained if the mounting for the cutters is so constructed that at least every two of their rotational axes intersect at a point beneath the drill head. In this case the points of the cutters come to lie nearer together than do their bases. The versions shown in the FIGS. 18–21 are particularly suited for such an inclined positioning of the axes, since there adjustment need be made only in the adapter and at the gear unit which connects the cutters. As far as the gearing is concerned it is sufficient to exchange the spur gears shown in the figures for corresponding bevel gears, this being very easy to do if the cogwheels, as shown in FIGS. 28a, 28c, and 28d, are mounted on shanks furnished with grooves or, in the lower region, with projections.

It is further possible to modify also the versions shown in the FIGS. 18–21, so that more than three cutters can be simultaneously driven with them. For this it is necessary only to provide mounts in the adapter for further shanks and to modify the gear unit as according to the FIGS. 6–12 or in a corresponding manner.

It is finally also possible to leave one or two cutters being held in the drill head in standstill while the other cutters rotate. The cutters standing still, at least one, or a corresponding space ranger being held with a shaft of the drill head can serve to guide the drill head, particularly in holes for bone cavities having already been previously made. As far as the gearing according to FIG. 17 as well as to FIGS. 19–21 is concerned, being attached on the outside of the drill head together with the cutters, it suffices to exchange the cutters which shouldn't rotate for corresponding cutters having no cogwheel on their upper end, or, in the case that the cogwheels are slipped on to the shanks as according to FIGS. 20a–20d, simply to pull the cogwheel off this cutter.

It is advisable, also when conventional drill heads are to be adapted by means of an adapter corresponding to FIGS. 18 ff. to the drill head according to the invention, to so construct the bore cylinder for accommodating the shank 8a, 8b of at least one cutter that this can be held in the drill head in several positions displaced with respect to one another in the direction of the rotational axis, its shank being provided with several annular tee-slots staggered in the direction of rotation. In this way, using a set of similar cutters, "dumbbell-like" bone cavities can be made, being of varying depth in the different regions.

There is a constructive measure here available, namely either to provide the cover of the conventional drill head, as according to the case exemplified in connection with FIG. 5a, with a continuous hole, or else to construct the additional bore cylinder, there being at least one, in the adapter for further cutters correspondinly long, or open at the top.

The bone drills 5a and 5b shown in FIG. 1 correspond to the first version of the drill which will now be more closely explained in a large number of variants by means of the FIGS. 22–33.

A bone cavity 7 is shown in a schematically presented jaw ridge 6 under the bone drills 5a and 5b, the bone cavity being formed by the bone drills 5a and 5b and exhibiting a "dumbbell-like" cross section. The shape of the bone cavity shows that the shanks 8a and 8b of the bone drills 5a and 5b are so positioned in the drill head that the distance A between their rotational axes 9a and 9b is smaller than the sum of the radii of the separate bone drills. The other bone drills according to the invention and according to the versions of FIGS. 34 ff. and its variants, and to the version of FIG. 41 and its variants can be employed in a corresponding way for the production of bone cavities with "dumbbell-like" cross section, if they are supported in a corresponding drill head where the distance A between the rotational axes is smaller than the sum of the maximal radii of the bone drills. It is naturally also possible to use the bone drills according to the invention beside each other in a correspondingly profiled drill head, or also to mount a larger number of such drills behind or beside each other, so that bone cavities with "double dumbbell-like" and "clover leaf-like" cross sections are created. In all cases the open construction of the bone drill enables an overlapping of the cutting surfaces. During the drilling operation a rinsing and cooling medium can be delivered by means of a nozzle 10 to the bone drills and the drilling area.

FIG. 22 shows the construction of the bone drill 5 as shown in FIG. 1, whereby a cutting head 111 is attached at the lower end of a conventional drill shank 8. The cutting head 111 consists of a series of round rods 112a . . . 112d, being coated with a layer of relatively coarse diamond dust at least on the regions facing outwards. The diamond coating is represented in the drawing by the dotted areas, as indicated by the reference symbol 113 in FIG. 22. It can be seen from the sectional view in FIG. 23 that 5 rods are circularly arranged in the cutting head 111. The outer surfaces with the diamond finish form the cutting surfaces of the cutting head. The rods traverse planes which contain the rotational axis 9 of the bone drill.

In the example shown in FIG. 22 the rods are bent inwards at the top and soldered or welded there as shown by the reference symbol 114. In the example of a drill as shown in FIG. 22 the rods run parallel downwards with a cylindric outer contour. At their ends they run together into a drill point, whereby care is taken that one cutting edge passes through the drill point.

If the rods are relatively thick as in the case of FIG. 23, the drill shank 8 does not need to run down through the cutting head 111. A basket-line lattice structure is thus created, being hollow inside, with large lateral perforations, which can be efficiently sprayed from the outside and above by a cooling agent which floods the borings out of the drilling region and the interior of the cutting head to the outside.

In the case of cutting heads tapering downwards rapidly in cross section, the rods can also taper in the direction of the drill point, this not being more clearly depicted in the drawing.

FIGS. 23-28 exemplify the possibilities for making heads 111 with varying numbers of rods.

In the example of FIG. 24 the arrangement of the rods corresponds to that of FIGS. 22 and 23, although in this case the drill shank 8 runs through the cutting head 111 so additionally reinforcing it.

In FIG. 25 the cutting head 111 is formed from 4 rods 115 being uniformly distributed and being of more sturdy construction than in the examples of FIG. 23 and FIG. 24. FIG. 25 exemplifies further the possibility of employing two similar drills for making "dumbbell-like" overlapping bone cavities, in that these are arranged with their rotational axes 9a and 9b at a distance A, this distance being less than the doubled radius r of the separate bone drills.

The possibility for overlapping of the drill holes is considerably dependent on the number of rods.

Whilst the use of, for example, 8 rods 116, distributed around the cutting head as shown in FIGS. 26 and 27, result in a considerably reduced overlapping as opposed to the example shown in FIG. 25, one obtains an even deeper overlapping of the drill holes when using bone drills which, according to FIG. 28, contain only three rods 117. However, the number of rods per cutting head should not be kept too small, since a more cylindrical bore is obtained with increasing numbers of rods.

In the version shown in FIG. 27 the cutting head is reinforced in the interior by means of three axially-running rods 118a, which are in place of shank 8. The breaking down of the shank into three separate rods reduces the danger of heat accumulating and improves the rinsing potential of the bone drill.

Figure 29:
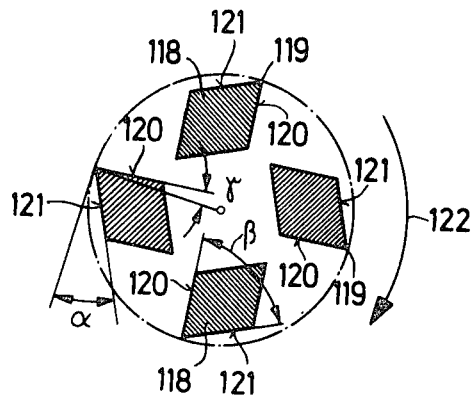
Figure 30:
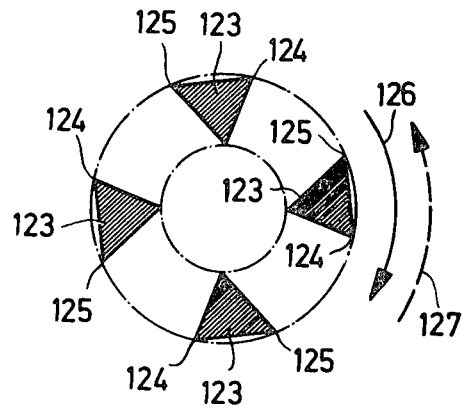
Figure 31:
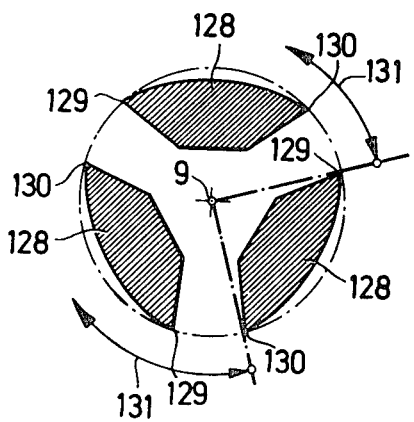

The FIGS. 29-31 show three further variants where rods with a quadrilateral cross section are used in place of round rods.

In the bone drill shown in cross section in FIG. 29, the rods 118 used are rhombic. The rods 118 are aligned asymmetrically, being so orientated that only one of their edges functions as a cutting edge 119. The use of this drill is limited to one cutting direction as indicated by the clockwise arrow 122. The true rakes 120 of the rods 118 have a small neg. rake angle $\alpha$. The open spaces 121 are constructed with a positive clearance angle $\alpha$. The front rake $\beta$ at the cutting edge 119 approaches 60°.

FIG. 30 shows the employment of rods 123 with a triangular profile. The rods are so arranged that their edges lie on two circles being concentric to the rotational axis of the cutting head. The outward-facing edge 124 is effective as cutting edge for the rotational direction 126, the outward-facing edge 125 for the rotational direction 127, whereby the corresponding rake angles vary and are in both cases positive. The bone drill indicated in cross section in FIG. 30 can thus be used in both rotational directions, having however a different cutting action in the two directions. Should the surfaces running inward from the cutting edges 124 and 125 of the rods 123 be equally broad, then one obtains equal rake angles and thus the same cutting action in both the rotational directions. The surfaces of the rods 123 lying between the cutting edges 124 and 125 can be constructed in a concave fashion, so that in each case both cutting edges produce a cutting effect in both rotational directions.

Similar cutting action in both rotational directions is obtained with the bone drill shown in cross section in FIG. 31, whose rods 128 have a cross section corresponding approximately to an equal-sided trapezium. The small base of the trapezium faces inwards in each case whilst the cutting edges 129 and 130 have the same rake angle for both cutting directions, indicated by the double-headed arrow 131.

In order to prevent a weakening of the cross section of the rod the long base of the trapezium, running between the edges 129 and 130 is bent outwards.

In the bone drill shown in FIG. 32 the upper ends of the rods 112 are bent inwards and, being staggered in the longitudinal direction, are welded bluntly onto the shaft 8, being continuous in this case. In this way a larger number of rods can be attached directly onto the shaft than would be possible if the rods were of the same height. In addition a good flow passage for a rinsing medium is obtained at the top side of the cutting head, the rinsing medium flowing in the case shown via a cylinder 132 in the interior of the shank 8 to an aperture 133 which opens out in the interior of the cutting head.

In order to attach a lead cylinder for the liquid in the interior of the cutting head, this must be sufficiently thick. This is however, not the case with the normal shanks commonly used in the dental field, having a diameter of 2.35 mm and the FG-shanks a diameter of 1.6 mm, which are generally used for this application of the bone drill.

In order to be sure, when using the bone drill for making overlapping drill holes according to FIG. 25, for example, that the drills are so held in the mounting of the corresponding drill heads as to orientate the rods of the one bone drill opposed to spaces of the other bone drill, the driving cams in the drill head, engaging with the ground down regions 134 at the upper ends of the drills, are correspondingly staggered. When making the bone drill itself care must be taken that the flattenings 134 or corresponding recesses assume exactly the same angular positions for the orientation of the rods.

The drill point is formed in the bone drill shown in FIG. 32 by the end of the rod 112d, this being bent at the bottom of the shank 8, so forming a cutting edge 135 running through the drill point. The ends of the other rods are blunt at the bottom, being firmly fixed to the rod 112d. This applies also for the rod 112c, which, simply for the clarification of the previously mentioned arrangement, is broken off at the bottom in FIG. 32.

FIG. 33a shows, partly in section, a further variant of the bone drill shown in FIG. 22, the upper end of the cutting head 111 here being constructed as a cogwheel 148, which accommodates the ends of the rods 112 and connects then with the shank 8. The outer edges of the rods 112, being inserted in the cogwheel 148, are flush with the top edges of the toothing 149, the rods thus forming a part of the toothing in the region of the cogwheel 148, this being especially apparent from FIG. 33b. FIG. 33b further shows the employment of two of the bone drills shown in FIG. 33a for the production of overlapping holes. The cogwheel 148 has in addition a number of continuous bore cylinders 150, through which, as indicated by arrow 150a, a cooling or rinsing agent can enter the interior of the cutting head.

FIG. 34 shows in a perspective, partly-broken presentation, a further bone drill 162, whose cutting head 163 consists of three thin, lamellar-like bits 164–166 standing out from the shank 8 and being orientated at 120° with respect to each other. The bits taper towards the drill point. The shank 8, which forms the shaft of the cutting head 163 in the upper region of same, tapers similarly in the direction of the drill point, through which one of the cutting edges runs. As shown in FIG. 35 the bits 164–166, standing out wing-like from the drill shaft, run curvedly with respect to the rotational direction, and each exhibit a cutting edge on the front side. The cutting edges lie in planes, at least in the upper region of the bone drill 162, which pass through the rotational axis 9. In the lower region, tapering strongly towards the drill point, the bits can also run round spirally. The bone drill 162 is constructed clockwise, as indicated by the arrow 170. For the production of overlapping bone cavities this bone drill is used in conjunction with a bone drill being homologous with respect to the cross sectional configuration, as shown in FIG. 40.

A modification of the bone drill 162 suitable both for a clockwise and an anticlockwise operation can be seen from the cross sectional presentation of FIG. 36. The bits 167–169 standing out wing-like from the drill shaft are each furnished with two cutting edges, which are symmetrical to their center plane running through the rotational axis, so that, with respect to the cutting edges, an arrangement arises similar to that shown in FIG. 31.

In order to reduce the danger of heat accumulation in the bone drill and also to improve the turbulence of the cooling medium introduced into the drill hole from above, the cutting head variant 163, as shown in FIG. 37, has a series of perforations 171 in the region of the bits 164–166.

FIG. 38 shows a further variant, in which case the cutting edges at the ends of the bits are provided with a toothing 172, 173, the toothings in the different bits being staggered. The bits can in addition, at least in their outer edge areas, be furnished with a diamond finish. For the driving of the bone drill as according to FIG. 40, each of the cutters can be provided as in FIG. 39 with a cogwheel 174, which is pushed onto the shank 8 and held there in such a manner that it can freely rotate. The diameter of the cogwheel 174 is smaller than the maximal radius of the cutting head 163. The shank 8 of the bone drill can, as shown in FIG. 39, be provided in a conventional way with an encircling annular tee-slot 175 at the upper end, by means of which tee-slot the drill is held in a drill head.

FIG. 41 shows a further bone drill, consisting of a thin-walled hollow body 176 being connected with the drill shanks 8, and which with respect to the outer contour corresponds in shape to the configuration of the desired drill hole, being however smaller than this dimensionally. The hollow body 176 has at the top a circular opening 177, this being limited on the interior by its wall 178. A mounting being connected to the drill shank 8 and consisting of 4 cross-shaped arms 179 standing out from the drill shank 8 and reaching to the walling 178 of the hollow body is inserted into the opening 177 in the example of FIG. 41.

The hollow body 176, preferably consisting of hardened sheet steel, is provided with a large number of openings 180 which permeate its surface in a sieve-like manner. The wall of the hollow body 176 is however not completely removed in the region of the openings 180, but is bent upwards, or respectively pushed through on the outside in the form of convexities, so that prominences 181 are formed, which with their free ends 182 forming cutting edges, stand up slantingly above the area of the openings 180. In the example shown in FIG. 41 the prominences 181 are made by providing U-shaped cuts, open to the right according to the drawing, in the hollow body 176. The area of the wall incorporated by the u-shaped cuts is bent upwards and outwards at the open side of the U, the front ends 182 of the prominences 181 being levelled off so that the free ends 182 are straight. The openings 180 and the accompanying prominences 181 are arranged around the extent of the hollow body 176 in circles 183, 184, 185 ... lying one under the other, whereby in each case the prominences 181 of one circle, eg. 184, lie opposite to gaps between the prominences of the neighbouring circle, eg. 183 resp. 185.

The consecutive prominences on the cutting head, in the longitudinal direction of same, lie in the upper regions of the hollow body in planes which pass through the rotational axis 9 of the bone drill. It is thus possible to employ two of the bone drills 141, the one being homologous to the drill shown in FIG. 41, for the production of "dumbbell-like" bone cavities, whereby the maximal overlapping of the cutting areas is determined by the height at which the prominences 181 stand out above the exterior surface of the hollow body 176. The described orientation of the prominences need not be maintained in the regions of the cutting head nearer to the drill point, where the radius of the hollow body 176 in these regions has decreased at least as much as the height of the prominences—that is, unless two corresponding bone drills with rotational axes downwardly coverging on each other are to be used. A cutting edge 186, which similarly can be formed by one of the previously-mentioned prominences, runs through the point of the cutting head. FIG. 42 shows unwound a variant of the hollow body 176. One can see how the prominences 181 are formed by bending up the wall 178 in the region of the openings 180.

FIG. 43 shows unwound a variant of the hollow body 176, where the prominences 181 are ground almost parallel to the wall 178.

FIG. 44 shows a variant of the hollow body 176, in which case this is formed from a corrugated-like material. FIG. 45 shows this unwound. The wall of the hollow body consists here of consecutive ridges 187 and troughs 188. The ridges 187 are inclined more steeply in the rotational direction than in the opposite direction. The hollow body formed of the corrugated-like material is provided in the region of its ridges with openings 189, over which prominences 190 stand. The prominences 190 are formed as in FIG. 41. The front edges of the prominences 190 form the cutting edges 191. When the bone drill rotates in the direction of the arrow 192, chips are sheared off the bone tissue 193, being shown by dotted shading, the chips passing out into the interior of the hollow body 176 from where they are subsequently rinsed out. In the example shown in FIGS. 44 and 45 only every second ridge 187 is provided in the previously-mentioned way with an opening 189 and a prominence 190 and constructed as a cutting edge 191. The prominences are distributed over the hollow body being displaced with respect to one another, as in FIG. 41. This means that that ridge 187, which in one of the circles 183–185 is not provided with a cutting edge 191, has a cutting edge 191 in both of the neighbouring rings.

FIG. 46 shows a longitudinal section through the bone drill shown in FIG. 41, in assembled form. The arrow 195 indicates the flow direction of a cooling- or rinsing medium which is introduced from the upper side into the hollow body 176.

FIG. 47 shows in section a possibility for the attachment of the hollow body on the drill shank 8. The drill shank 8 forms a cogwheel 197, being provided with a through bore cylinder 196, at its lower end. The cogwheel 197 has at its lower end a flange, onto which the upper edge of the hollow body 176 is pushed or keyed.

In a further variant, shown in FIG. 48, the hollow body 176 is attached bluntly to a plate 199 which has through bore cylinders 200 and forms the lower end of the drill shank 8.

FIG. 49 shows a variant of the bone drill described in FIG. 48 ff., which enables a larger overlapping of the "dumbbell-like" bone cavities formed with a pair of these drills. The bone drills 201a resp. 201b consist in the upper region of the cutting head of several curved, preferably circular arc segments 202a resp. 203a, which exhibit the same structure as the hollow body 176 in the preceding examples. The segments 202a resp. 203a, distributed around the extent of the cutting head in numbers of 2 to 4, account for ½ to ⅓ of the cutting head circumference. Between the individual segments there are cutaway portions 206a resp. 206b, so that the segments of the corresponding but contra-rotating bone drills 201a and 201b can interlock in these cutaway portions. The segment-like construction can extend down to the drill point, this being essential in the case of cylindrical bone drills. In the case of bone drills tapering conically, the lower region 204a, 204b of the cutting head, as shown in FIG. 49, is constructed as a rotationally symmetric hollow body corresponding to the representation in FIG. 41, or else is provided with cutting edges distributed over the entire surface.

The cutting heads in the case shown are attached at the upper ends of the segments 202a, 202b to the lower ends of the drill shanks 8a resp. 8b via spokes 203a resp. 203b resembling sectors of circles. If the drill shanks 8a, 8b reach further down into the interior of the cutting head, the spokes 203a, 203b, or other corresponding connecting elements, can also be moved further down, this being favourable for the entry of a rinsing- and cooling medium into the cutting heads. The spokes 203a resp. 203b are provided in the case shown with through bore cylinders 207a resp. 207b. The drill shanks 8a resp. 8b engage with the driving mechanism of the drill head or respectively with corresponding cogwheels in a form-locking manner via the grooves 147. For this the grooves 147, as in the case of the previously-described further variants of the bone drill, are positioned in the drill shanks in such a way that when the two bone drills 201a and 201b are inserted in a corresponding drill head they automatically assume a position whereby the segments 202a resp. 202b of the one bone drill interlock in the cutaway positions 206a resp. 206b of the other bone drill. The drill shanks 8a, 8b are in addition provided with a series of encircling annular tee-slots 205a resp. 205b, preferably lying above one another at equidistant intervals, into which corresponding mounting elements of the drill head can grip. The annular tee-slots 205a resp. 205b enable the individual bone drills to be mounted at different depths in the drill head 4. When simultaneously using at least two corresponding bone drills in the drill head, the drills being mounted at tee-slots 205a and 205b of different heights, varying "dumbbell-like" bone cavities can be bored with the same drills, the cavities being of varying depth at different points. For reasons of the irregularity of the jawbone and the nerves and vessels running in it this is often desirable. The slots have preferably a depth of about 0.4 mm, a breadth of about 0.8 mm and are separated from one another at intervals of about 2 mm to about 4 mm.

The following explanations concern the enossal dental half-implant according to the invention.

Since the EDH according to the invention has basically to do with the endostructure, while as exostructure any sort of conventional tooth or bridge construction matching the neighbouring teeth in each case can be used, the FIGS. 50–59 show in each case only the endostructure of the EDHs. The length L of the endostructure corresponds to at least the depth of the bone cavity bored in the jawbone and being intended to accommodate it. It is generally larger than this, since it is possible to reduce the EDHs by removal of material on the top side to the desired length or to trim it with a diamond-grinding body such that at least a pin or a peg for the mounting of the tooth substitute remains.

The endostructure 301 of the EDH shown in FIG. 50 consists of two cone-like regions 302 and 303 overlapping in their upper ⅓. The cone-like regions 302 and 303 consist in the case shown of two similar circular cones, which in the region where the endostructure extrudes from the jawbone—ie. at the upper end—as can be seen from FIG. 51, exhibit the diameter D and are superimposed there for a stretch Ü along the connecting line through the exit points of their axes 304 and 305. The circular cones are rounded at their lower ends in such a way that the cone-like regions taper conically for approximately ¾ to approximately ⅔ of their length, then being shaped cylindrically at their lower ends over some ¼ to ⅓ of their length. In the case shown the overlap Ü fits the relation:

$$Ü = 0.17 \times D.$$

The relation between D and L is approximately 1:2,5. The axes 304 and 305 of the cone-like regions lie in one plane and run parallel to one another. The inner edges 306 and 307 formed where the cone-shaped shells of the two cone-like regions intersect are rounded off, as is also the point 308 created at the lower end of the overlapping regions. The broken-lined circles 309 and 310 in FIG. 51 indicate the lower ends of the circular cone stumps at the point where the rounding off of the lower ends of the cone-like regions begins. It can be seen from FIG. 51 that for the diameter d of these circles the relation:

$$d = D - 2Ü$$

approximately fits. The diameter d of the circles 309 and 310 corresponds also essentially to the axis diameter of special bone drills according to the invention as shown in the FIGS. 22–49. These are held pairwise and at a distance corresponding to that between the axes 304 and 305 in a drill head as previously shown in the FIGS. 1–21 in such a way that their cutting areas overlap. By means of this arrangement according to the invention it is possible through simple sinking to produce a bone cavity in the jaw bone for the insertion of the EDH, the outer contour of the bone cavity corresponding exactly to the outer contour of the EDH.

The endostructure shown in the FIGS. 52 and 53 corresponds essentially to the versions shown in the FIGS. 50 and 51, whereby in addition to the two overlapping cone-like regions 302 and 303 a corresponding similar third cone-like region 311 is provided, this being positioned laterally to the cone-like region 303. In the case shown, the axis 312 of the third cone-like region 311 is parallel to the axes 304 and 305 of the first two cone-like regions 302 and 303. However the axis 312 no longer lies in the plane formed by the axes 304 and 305, being laterally displaced to this, so that the cross section of the endostructure—seen from FIG. 53—curves slightly downwards. This curving of the endostructure enables the EDH to be adapted to the curve of the mandibular arch.

FIG. 54 shows a top view of a further development of the version shown in FIGS. 52 and 53, whereby a third cone-like region 313 with an axis 314 is arranged laterally to the overlapping cone-like regions 302 and 303 with the axes 304 and 305 in such a way that it overlaps with the second cone-like region 303 whilst just touching the first cone-like region 302 at a point laterally or along a straight line. The edges and points formed at the intersections and the contact points are rounded off. In principle one can also position the third cone-like region 313 in such a way that an additional overlap with the first cone-like region 302 results, so that the exit points of the axes 304, 305 and 314 can possibly form an equilateral triangle. However the version shown in FIG. 54 is preferable for practical reasons, since in this case the production of a corresponding bone cavity in one operation is still possible, through sinking, by means of three drills overlapping in their cutting regions and being held in a corresponding drill head. This is not possible for an endostructure where the center points of the three mutually overlapping cone-like regions correspond to the corner points of an equilateral triangle, since in this case the three drills for the production of the corresponding bone cavity would in each case have to interlock pair-wise with their cutters, this only being possible when the two drills of a pair are driven contra-rotating.

The endostructure shown in the FIGS. 52–54 can be extended by the addition of further cone-like regions, this occurring in a corresponding manner and not being depicted more closely in the drawings. Such an endostructure consisting of four or more cone-like regions is suitable for the insertion of bridge constructions in largely toothless jaws. In normal cases however endostructures with two or three cone-like regions are sufficient for a safe retention of the EDH.

The parallel alignment of the axes 304, 305, 312 and 314 are used in the previously-described versions effects in the case of the cone-like regions with conical outer surfaces an approximately uniform transmission of force to all areas of the wall of the jawbone surrounding the endostructure. In some cases it is useful however to deviate from this arrangement being for reasons of the force transmission seemingly favourable, and to incline the axes of the individual cone-like regions with respect to each other, as for example is shown in the FIGS. 55 and 56.

The endostructure 315 shown in the upper part of FIG. 55 contains two cone-like regions 316, 317, whose axes, 318, 319 are so inclined that they intersect in a pointed angle $\alpha_1$ beneath the endostructure. This means that the two cone-like regions 316 and 317 overlap until shortly above their lower ends. To accomodate this endostructure being particularly suitable as tooth root substitute for inciser and eye teeth, bone cavities 321 whose outer contour exactly matches the outer contour of the endostructure 315 can be made in a jawbone 320 by simple sinking, as shown in the lower part of FIG. 55, using a corresponding drill pair, whose axes of rotation also enclose an angle $\alpha_1$. The arrows 322 indicate the direction with which the drills are sunk into the bone, as well as the direction with which the implant is subsequently embedded in the bone cavity 321.

In the arrangement of the endostructure 323 shown in FIG. 56, the two cone-like regions 324 and 325 are so inclined with respect to each other that their axes 326, 327 intersect above the endostructure in a pointed angle $\alpha_a$. Thus the two cone-like regions 324 and 325 overlap only in a small upper piece, meaning that between their lower ends a V-shaped space 328 is formed reaching a long way upwards. The endostructure 323 is intended in particular for those cases, where, as shown underneath in FIG. 56, a nerve or a vessel 329 runs in the bone tissue 320 of the jawbone at such a shallow depth that an implant according to prior art could not be inserted there at all, and an implant according to the FIGS. 50–52 only with some risk. Even if the bone tissue under the middle of the implant to be inserted is cancellous, the use of an endostructure according to FIG. 56 can be of advantage.

The following table gives a further example for a set of such EDHs. The top line with the values D indicates the maximal diameters of the cone-like regions of the endostructure while in the lines underneath, the lengths L in mm are given in each case for the type of endostructure as indicated on the left.

| Type of endostructure | D | | | | | | |
|---|---|---|---|---|---|---|---|
| | 3,0 | 3,5 | 4,0 | 4,5 | 5 | 6 | 8 |
| bumbbell acc. FIG. 51 | | L = 13 | | L = 15 and L = 20 | | L = 15 and L = 20 | L = 15 |
| double-dumbbell acc. FIG. 53 | | L = 15 | | L = 15 | | L = 15 | L = 15 |
| tertiary arrangement acc. FIG. 54 | L = 15 | | | L = 15 and L = 20 | L = 15 | | |

Since it is of particular advantage when implanting the respective EDHs if the accompanying bone cavity 330 can be made by simple sinking with a corresponding special tool, the angle $\alpha_a$ between the axes 326 and 327 should not be chosen larger than the sum of the angles $\beta_1$ and $\beta_2$ which the cone-shaped shells 331 and 332 enclose with the accompanying axes 326 and 327. This means, as seen from FIG. 56, that the outermost shell contours run approximately parallel to one another.

In the endostructures 315 and 323 the intersection edges and points have been rounded off.

The axes 318 and 319 resp. 326 and 327 of the cone-like regions lie in each case in a plane which coincides with the drawing plane of the FIGS. 55 and 56. This is useful although not absolutely necessary. One can orientate the cone-like regions at such angles to one another that their axes intersect the drawing plane. (This applies also for the versions of FIGS. 50–54) The lines 304, 305, 312 resp. 318 and 319 or 326, 327 would then be projections of these axes, which run forwards or backwards out of the drawing plane, when one puts the exit points of the axes in this plane.

The endostructures shown in the previous figures were formed in each case from similar, rotationally symmetric cone-like regions. It is however possible using methods already described, to combine varying cone-like regions into the endostructures, whereby the diameter D, the lengths L and the angle between the axes and the cone-shaped shell can vary. Also in these cases a production of exactly-matching bone cavities through simple sinking is possible using a choice of corresponding drills.

It is finally also possible to design the cross section of the cone-like region oval or elliptical instead of circular, as in the previously described examples, although in this case it is no longer possible to produce corresponding bone cavities through simple sinking with simple tools. The angle $\beta$ between the axial direction and the shell walls should however always lie between 4° and 15°, whatever cross sectional surface is chosen for the cone-like regions.

The FIGS. 57, 58 and 59 show in longitudinal section different variants of the cone-like regions with varying lengths L, diameter D and angles $\beta$. The indices to the letters L, l, D, d given in brackets indicate examples of measurements in mm for a set of cone-like regions of endostructures which are suitable for EDHs in the human field. The angle $\beta$ bounded by the cone-shaped shells and the axes is given in each case in degrees.

The FIGS. 60–63 exemplify some possibilities for the attachment of a tooth suprastructure onto the endostructure.

Figure 60:
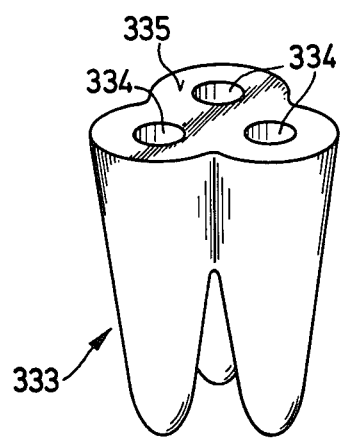

The endostructure 333 shown in FIG. 60 consisting of three cone-like regions with their axes arranged in a triangle have three bore cylinders 334 approximately central to the axes of the individual cone-like regions, which can be provided with an internal thread. The bore cylinders 334 serve to accommodate pegs or screws, not indicated, which carry the crown construction. This endostructure is suitable particularly for a two-stage implantation, in which case the surface 335 is sewn over with oral mucosa having been folded back before beginning the implantation, until the region of the implant has healed. The bore cylinders 334 can also serve for the temporary accommodation of supporting pins with which the EDHs can be fixed to the neighbouring teeth until the tooth suprastructure is mounted.

Figure 61:
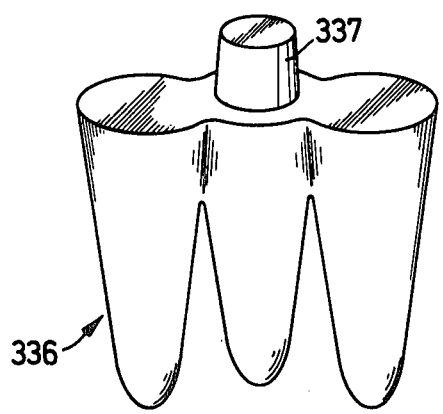

FIG. 61 shows a double dumbbell-like endostructure 336 having a single peg 337 on its upper surface for the attachment of the suprastructure.

Figure 62:
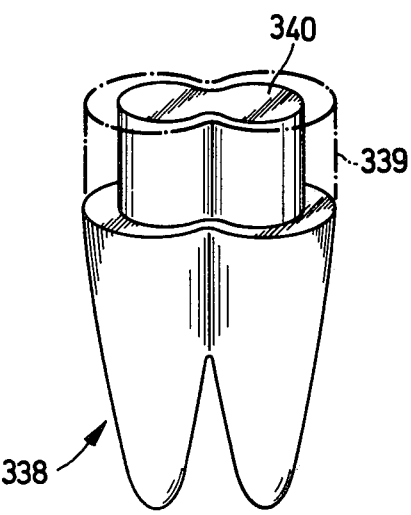

FIG. 62 shows a dumbbell-like endostructure 338, which originally exhibited the larger dimension 339 at the top, as indicated by the dot-dash line. By means of trimming with a suitable diamond cutter the two cone-like regions in this upper piece 339 are ground down so far as to leave only the dumbbell-like peg 340 remaining, this being intended for the attachment of the tooth suprastructure. Since the peg 340 should have a height of some 8 mm, it is advisable to construct the endostructure 338 longer by this amount from the start.

Figure 63:
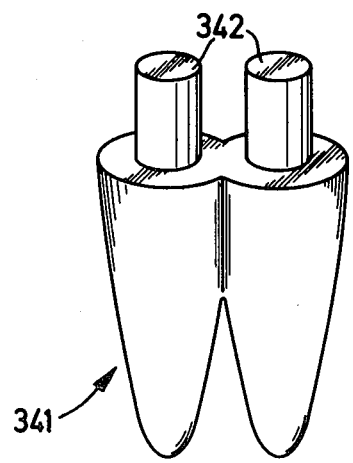

The dumbbell-like endostructure 341 shown in FIG. 63 is provided with two pegs 342 intended for the attachment of a tooth suprastructure.

Besides the previously-mentioned attachment possibilities for the suprastructure there are naturally a large number of further attachment constructions for the varying endostructures according to the invention which can be used.

The longitudinal section through an EDH in FIG. 64 shows an example for the internal construction of the cone-like regions of an endostructure. It shows at the same time an example for a construction of the EDH whereby the suprastructure exhibiting a crown is produced as a finished tooth suprastructure in one piece with the endostructure. The EDH is made up of different layer surrounding each other in a way corresponding to that with which by means of conventional porcelain techniques or metal ceramic techniques dental prosthetic elements are produced.

When seen from the interior to the exterior, the EDH 342 consists of a core substance 343, in which a reinforcement element 344 can if necessary be embedded. The core substance is surrounded on the exterior by a dentine substance 345, onto which in the region of the endostructure a porous surface layer 346 is applied. The layer 346, which exhibits preferably a thickness of some 0.3–0.5 mm, is permeated by a large number of vacuoles which enable an ingrowth of a bone tissue when the endostructure 347 is implanted in a synthetic tooth cavity of the jaw.

Along the length of the endostructure 347 there are equidistant markings 348 provided in the porous surface layer 346, these markings consisting in the case shown of encircling grooves.

The suprastructure 349 forming the crown region of the EDH corresponds in its internal make-up essentially to the make-up of the endostructure 347. It differs from this only in that in place of the porous surface layer 346, a layer 350 consisting of an enamel substance and possibly a layer 351 consisting of a glazing substance is applied. Naturally the EDH 342 can also be furnished in the region of the exostructure 349 in familiar ways with substances and/or with colouring materials which enable the EDH to be optimally matched with the neighbouring natural teeth in the dentition.

The production of the EDH follows according to methods common in the dental field, whereby the porous surface layer 346, eventually with the enamel and the glazing layers, is applied last of all. It is however also possible to fire the layer 346 on at the same time as the layer 345. The use of a porcelain press technique is also possible (see eg. the magazine "Zahnärztliche Welt/Rundschau", journal 15, 78. volume 1969, pgs. 682–687, and the magazine "Das Dentallabor" Journal 8/1970 as well as the professional journal of the schweizerischen Zahntechnikervereinigung "Die Zahntechnik" No. 1/1969).

Examples of the porous surface layer 346, for the makeup of the EDHs using different materials and press techniques are also described by the same applicant in the patent application, to which reference is here made, namely: Ser. No. 778,284.

I claim:

1. An enossal dental half-implant suitable for use in at least two simultaneously drilled, identical, uniformly shaped, overlapping bores in a jaw bone, said implant having a downwardly tapering endostructure having an upper end and a lower end constructed as a dental root substitute comprising a unitary one-piece structure having at least two identical, uniformly shaped cone-like root portions which overlap at least at the upper end of said endostructure and which are separate from each other at the lower end of said endostructure, said upper end of said endostructure having a uniformly lobed cross-sectional configuration lying in a plane having the greatest cross-sectional area of the endostructure while the entire cone-like root portions are disposed completely within a projection of said greatest cross-sectional area in a direction perpendicular to said plane of said upper end.

2. An enossal dental half-implant as set forth in claim 1 wherein each of said cone-like regions are circular in cross-section with the said greatest cross-sectional area in the region of overlap having a dumbbell configuration when two uniform root portions overlap.

3. An enossal dental half-implant as set forth in claim 2 wherein the center points of the cross-sectional areas of the cone-like portions lie on straight lines which form the axes of said cone-like portions with the sides of said cone-like portions being limited by conical surfaces.

4. An enossal dental half-implant as set forth in claim 3 wherein said axes extend parallel to each other.

5. An enossal dental half-implant as set forth in claim 3 wherein said axes are inclined relative to each other and intersect each other.

6. An enossal dental half-implant as set forth in claim 5 wherein said axes intersect below the lower end of said endostructure.

7. An enossal dental half-implant as set forth in claim 5 wherein said axes intersect above the upper end of said endostructure.

8. An enossal dental half-implant as set forth in claim 3 wherein said axes lie in a common plane.

9. An enossal dental half-implant as set forth in claim 1 wherein said endostructure includes three cone-like portions disposed in a triangle beside each other with two of said cone-like regions touching each other while at the same time intersecting a third cone-like portion at the upper end of said endostructure.

10. An enossal dental half-implant as set forth in claim 1 further comprising an exostructure wherein the contour of the endostructure at the upper end of said endostructure is extended upwardly into said exostructure.

11. An enossal dental half-implant according to claim 10 wherein at least said endostructure is provided with circumferential grooves about said cone-like root portions and a porous surface layer.

12. An enossal dental half-implant according to claim 10 wherein said exostructure is formed at the upper portion thereof in a tooth-like configuration.

* * * * *